(12) United States Patent
Takayama et al.

(10) Patent No.: US 8,865,464 B2
(45) Date of Patent: Oct. 21, 2014

(54) MICROFLUIDIC CELL CULTURE DEVICE

(75) Inventors: Shuichi Takayama, Ann Arbor, MI (US); Lourdes Marcella Cabrera, Ann Arbor, MI (US); Yun Seok Heo, Ann Arbor, MI (US); Gary Daniel Smith, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/854,465

(22) Filed: Aug. 11, 2010

(65) Prior Publication Data

US 2010/0323439 A1 Dec. 23, 2010

Related U.S. Application Data

(62) Division of application No. 11/582,027, filed on Oct. 17, 2006, now abandoned.

(60) Provisional application No. 60/727,934, filed on Oct. 18, 2005, provisional application No. 60/728,030, filed on Oct. 18, 2005, provisional application No. 60/741,665, filed on Dec. 2, 2005, provisional application No. 60/741,864, filed on Dec. 2, 2005, provisional application No. 60/802,705, filed on May 23, 2006, provisional application No. 60/812,166, filed on Jun. 9, 2006.

(51) Int. Cl.
| | |
|---|---|
| C12N 5/07 | (2010.01) |
| C12N 5/16 | (2006.01) |
| C12N 5/00 | (2006.01) |
| C12M 1/00 | (2006.01) |
| C12M 3/06 | (2006.01) |
| B01L 3/00 | (2006.01) |

(52) U.S. Cl.
CPC ............. *C12N 5/0075* (2013.01); *C12M 23/34* (2013.01); *C12M 23/16* (2013.01); *B01L 3/5085* (2013.01); *B01L 3/5027* (2013.01)
USPC ......................... 435/326; 435/287.2; 435/325

(58) Field of Classification Search
CPC ....... A61K 38/00; A61K 48/00; A61K 35/12; A01K 2217/05; C07K 2319/00; C12N 2310/121; C12N 15/113; A61B 17/435; A61D 19/04; B01L 3/502761; B01L 3/5025; B01L 2300/0887; B01L 2300/0684; B01L 2300/0864; B01L 2200/0668
USPC ....................................... 435/287.2, 325, 366
See application file for complete search history.

(56) References Cited

U.S. PATENT DOCUMENTS

| | | |
|---|---|---|
| 4,574,000 A | 3/1986 | Hunter |
| 6,193,647 B1 | 2/2001 | Beebe et al. |

(Continued)

FOREIGN PATENT DOCUMENTS

| | | | |
|---|---|---|---|
| JP | H10-084942 | 4/1998 | |
| JP | 2002153260 A | * 5/2002 | ............... C12M 1/34 |

(Continued)

OTHER PUBLICATIONS

Japanese Patent Application No. 2005-204837 (Kohyo), English translation of Abstract.

(Continued)

*Primary Examiner* — Michael Hobbs
(74) *Attorney, Agent, or Firm* — Casimir Jones SC

(57) ABSTRACT

Microfluidic devices for cell culturing and methods for using the same are disclosed. One device includes a substrate and membrane. The substrate includes a reservoir in fluid communication with a passage. A bio-compatible fluid may be added to the reservoir and passage. The reservoir is configured to receive and retain at least a portion of a cell mass. The membrane acts as a barrier to evaporation of the bio-compatible fluid from the passage. A cover fluid may be added to cover the bio-compatible fluid to prevent evaporation of the bio-compatible fluid.

13 Claims, 6 Drawing Sheets

(56) References Cited

U.S. PATENT DOCUMENTS

| | | | |
|---|---|---|---|
| 6,448,069 B1 | 9/2002 | Cecchi et al. | |
| 6,673,008 B1 | 1/2004 | Thompson et al. | |
| 6,695,765 B1 | 2/2004 | Beebe et al. | |
| 6,807,892 B2 | 10/2004 | Biegelsen et al. | |
| 2002/0068358 A1 | 6/2002 | Campbell et al. | |
| 2002/0182627 A1* | 12/2002 | Wang et al. | 435/6 |
| 2003/0003570 A1 | 1/2003 | Kanegasaki et al. | |
| 2003/0003571 A1 | 1/2003 | Kanegasaki et al. | |
| 2005/0141344 A1* | 6/2005 | Ekstrand et al. | 366/341 |

FOREIGN PATENT DOCUMENTS

| | | | | |
|---|---|---|---|---|
| JP | 2002177364 A | | 6/2002 | |
| JP | 2003088357 A | * | 3/2003 | C12M 1/32 |
| JP | 2003180336 A | * | 7/2003 | C12M 3/00 |
| JP | 2003533221 A | * | 11/2003 | C12M 1/00 |
| JP | 2004502929 A | * | 1/2004 | G01N 33/53 |
| JP | 2004532003 A | * | 10/2004 | C12Q 1/88 |
| JP | 2005080607 | | 3/2005 | |
| JP | 2005204837 A | * | 8/2005 | A61M 5/14 |
| JP | 2007504816 | | 11/2006 | |
| JP | 2006527093 | | 3/2007 | |
| JP | 2007504816 A | * | 3/2007 | C12M 3/00 |
| WO | 2004018654 | | 3/2004 | |
| WO | 2005023124 | | 3/2004 | |
| WO | 2004034053 A2 | | 4/2004 | |
| WO | 2005023124 A2 | | 3/2005 | |
| WO | 2005046620 | | 5/2005 | |
| WO | 2005050754 | | 6/2005 | |
| WO | WO2006/089354 | | 8/2006 | |
| WO | 2007047772 A | | 4/2007 | |
| WO | WO 2007/047825 A | | 4/2007 | |
| WO | WO 2007/047826 A | | 4/2007 | |
| WO | WO 2008/108746 A | | 9/2008 | |

OTHER PUBLICATIONS

Japanese Patent Application No. 2003-533221 (Koyho), English translation of Abstract.
Japanese Patent Application No. 2003-088357 (Koyho), English translation of Abstract.
Japanese Patent Application No. 2004-532003 (Koyho), English translation of Abstract.
Japanese Patent Application No. 2003180336 (Kokai), English translation of Abstract.
Japanese Patent Application No. 2004502929 (Koyho), English translation of Abstract.
Japanese Patent Application No. 2007-504816 (Koyho), English translation of Abstract.
Japanese Patent Application No. 2002-153260 (Koyho), English translation of Abstract.
R.S. Suh, N. Phadke, D.A. Ohl, S. Takayama, and G. D. Smith, Rethinking gamete/embryo isolation and culture with microfluidics, Human Reproduction Update, vol. 9, No. 5, 2003, pp. 451-461.
Figeys and D. Pinto, Lab-on-a-Chip: A Revolution in Biological and Medical Sciences, Analytical Chemistry, May 1, 2000, pp. 330A-335A.
N.A. Polson and M.A. Hayes, Microfluidics Controlling Fluids in Small Places, Analytical Chemistry, Jun. 1, 2001, pp. 312A-319A.
W. Gu, X. Zhu, N. Futai, B.S. Cho, and S. Takayama, Computerized microfluidic cell culture using elastomeric channels and Braille displays, PNAS, vol. 101, No. 45, Nov. 9, 2004, pp. 15861-15866.
Verneuil, A Buguin and P. Silberzan, Permeation-induced flows: Consequences for silicon-based microfluidics, Europhysics Letters, 68(3), Nov. 1, 2004, pp. 412-418.
D.C. Duffy, J.C. McDonald, O.J.A. Schueller, and G.M. Whitesides, Rapid Prototyping of Microfluidic Systems in Poly(dimethylsiloxane), Anal. Chem., vol. 70, No. 23, Dec. 1, 1998, pp. 4974-4984.
N. Futai, W. Gu, and S. Takayama, Rapid Prototyping of Microstructures with Bell-Shaped Cross-Sections and Its Application to Deformation-Based Microfluidic Valves, Adv. Mater., 16, No. 15, Aug. 4, 2004, pp. 1320-1323.

A. Vander, J. Sherman, and D. Luciano, Human physiology 8$^{th}$ edition, McGraw Hill, pp. 132-134.
R.N. Borland, S. Hazra, J.D. Biggers, and C.P. Lechene, The elemental composition of the environments of the gametes and preimplantation embryo during the initiation of pregnancy.
A. Davidson, M. Vermesh, R.A. Lobo, and R.J. Paulson, The Temporal Effects of Changes in in Vitro Fertilization Culture Media on the One-Cell Mouse Embryo System, Journal of in Vitro Fertilization and Embryo Transfer, vol. 5, No. 3, 1988, pp. 149-152.
A. Hay-Schmidt, The Influence of Osmolality on Mouse Two-Cell Development, Journal of Assisted Reproduction and Genetics, vol. 10, No. 1, 1993, pp. 95-98.
J.D. Biggers, J.A. Lawitts, and C.P. Lechene, The Protective Action of Betaine on the Deleterious Effects of NaCl on Preimplantation Mouse Embryos In Vitro, Molecular Reproduction and Development 34, 1993, pp. 380-390.
K.M. Dawson and J.M. Baltz, Organic Osmolytes and Embryos: Substrates of the Gly and $\beta$ Transport Systems Protect Mouse Zygotes against the Effects of Raised Osmolarity, Biology of Reproduction 56, 1997, pp. 1550-1558.
Y.S. Shin, K. Cho, S.H. Lim, S. Chung, S.-J. Park, C. Chung, D.-C. Han, and J.K. Chang, PDMS-based micro PCR chip with Parylene coating, J. Micromech. Microeng. 13, Jun. 20, 2003, pp. 768-774.
G. Diaz, R. Isola, A.M. Falchi, and A. Diana, $CO_2$-Enriched Atmosphere on the Microscope Stage, BioTechniques 27, Aug. 1999, pp. 292-294.
C.-L. Ho, T.Y. Mou, P.S. Chiang, C.-L. Weng, and N.-H. Chow, Mini chamber system for long-term maintenance and observation of cultured cells, BioTechniques 38, Feb. 2005, pp. 267-273.
A. Prokop, Z. Prokop, D. Schaffer, E. Kozlov, J. Wikswo, D. Cliffel, and F. Baudenbacher, NanoLiterBioReactor: Long-Term Mammalian Cell Culture at Nanofabricated Scale, Biomedical Microdevices, 6, 2004, pp. 325-339.
A. Tourovskaia, X. Figueroa-Masot, and A. Folch, Differentiation-on-a-chip: A microfluidic platform for long-term cell culture studies, Lab Chip, 5, Jul. 26, 2004, pp. 14-19.
E. Leclerc, Y. Sakai, and T. Fujii, Perfusion culture of fetal human hepatocytes in microfluidic environments, Biochemical Engineering Journal 20, 2004, pp. 143-148.
P.J. Hung, P.J. Lee, P. Sabounchi, R. Lin, and L.P. Lee, Continuous Perfusion Microfluidic Cell Culture Array for High-Throughput Cell-Based Assays, Biotechnology and Bioengineering, vol. 89, No. 1, Jan. 5, 2005, pp. 1-7.
A. Itagaki and G. Kimura, Tes and Hepes Buffers in Mammalian Cell Cultures and Viral Studies: Problem of Carbon Dioxide Requirement, Exptl Cell Res 83 (1974), pp. 351-361.
A. Leibovitz, The Growth and Maintenance of Tissue-Cell Cultures in Free Gas Exchange With the Atmosphere, AmJ.Hyg., vol. 78, Mar. 23, 1963, pp. 173-180.
W.H. Siegel, Examining the Relationship Between Media and Light, Biopharm 13.1, Jan. 2000, pp. 65-68.
G.M. Walker, H.C. Zeringue, and D.J. Beebe, Microenvironment design considerations for cellular scale studies, Lap Chip, Feb. 10, 2004, 4, pp. 91-97.
P. Clark, G.A. Dunn, A. Knibbs, and M. Peckham, Alignment of myoblasts on ultrafine gratings inhibits fusion in vitro, The International Journal of Biochemistry & Cell Biology, 34, 2002, pp. 816-825.
K.H. Gilchrist, V.N. Barker, L.E. Fletcher, B.D. DeBusschere, P. Ghanouni, L. Giovangrandi, and G.T.A. Kovacs, General purpose, field-portable cell-based biosensor platform, Biosensors & Bioelectronics, 16 (2001), 557-564.
S.K.W. Dertinger, D.T. Chiu, N.L. Jeon, and G.M. Whitesides, Generation of Gradients Having Complex Shapes Using Microfluidic Networks, Analytical Chemistry, vol. 73, No. 6, Mar. 15, 2001, pp. 1240-1246.
S. Takayama, E. Ostuni, P. LeDuc, K. Naruse, D.E. Ingber, and G.M. Whitesides, Subcellular positioning of small molecules, Nature, vol. 411, Jun. 28, 2001, p. 1016.
Zhu, L.Y. Chu, B.-H. Chueh, M. Shen, B. Hazarika, N. Phadke, and S. Takayama, Analyst, 129, Aug. 11, 2004, pp. 1026-1031.
S.R. Quake and A. Scherer, From Micro- to Nanofabrication with Soft Materials, Science, vol. 290, Nov. 24, 2000, pp. 1536-1540.

(56) References Cited

OTHER PUBLICATIONS

T.J. Johnson, D. Ross, M. Gaitan, and L.E. Locascio, Laser Modification of Preformed Polymer Microchannels: Application to Reduce Band Broadening around Turns Subject to Electrokinetic Flow, Analytical Chemistry, vol. 73, No. 15, Aug. 1, 2001, pp. 3656-3661.

A.N. Moor, R. Murtazina and L. Fliegel, Calcium and Osmotic Regulation of the $Na^+/H^+$ Exchanger in Neonatal Ventricular Myocytes, J Mol Cell Cardiol 31, 2000, pp. 925-936.

W. Zhou, C.-C. Chen, B. Buckland, and J. Aunins, Fed-Batch Culture of Recombinant NSO Myeloma Cells with High Monoclonal Antibody Production, Biotechnology and Bioengineereing, vol. 55, No. 5, Sep. 5, 1997, pp. 783-792.

S.S. Ozturk and B.O. Palsson, Effect of Medium Osmolarity on Hybridoma Growth, Metabolism, and Antibody Production, Biotechnology and Bioengineering, vol. 37, Apr. 1991, pp. 989-993.

N. Takagi, H. Hayashi, and T. Yoshida, The effect of osmolarity on metabolism and morphology in adhesion and suspension chinese hamster ovary cells producing tissue plasminogen activator, Cytotechnology, 29, 2000, pp. 171-179.

J. Lin, M. Takagi, Y. Qu, P. Gao, and T. Yoshida, Enhanced monoclonal antibody production by gradual increase of osmotic pressure, Cytotechnology, 29, 1999, pp. 27-33.

M.-H. Wu, G. Dimopoulos, A. Mantalaris, and J. Varley, The effect of hyperosmotic pressure on antibody production and gene expression in the GS-NSO cell line, Biotechnol. Appl. Biochem., 40, 2004, pp. 41-46.

R.L. Brinster, Studies on the Development of Mouse Embyros in Vitro, J. Exp. Zool., 158, Feb. 1965, pp. 69-78.

B. Zheng, L.S. Roach, and R.F. Ismagilov, Screening of Protein Crystallization Conditions on a Microfluidic Chip Using Nanoliter-Size Droplets, J. Am. Chem. Soc., 125, Aug. 23, 2003, pp. 11170-11171.

C.G. Koh, W. Tan, M.Q. Zhao, A.J. Ricco, Z.H. Fan, Integrating Polymerase Chain Reaction, Valving, and Electrophoresis in a Plastic Device for Bacterial Detection, Analytical Chemistry, vol. 75, No. 17, Sep. 1, 2003, pp. 4591-4598.

Z. Zhao, Z. Cui, D. Cui, and S. Xia, Monolithically integrated PCR biochip for DNA amplification, Sensors and Actuators A 108, 2003, pp. 162-167.

J. Khandurina, T.E. McKnight, S.C. Jacobson, L.C. Waters, R.S. Foote, and J.M. Ramsey, Integrated System for Rapid PCR-Based DNA Analysis in Microfluidic Devices, Analytical Chemistry, vol. 72, No. 13, Jul. 1, 2000, pp. 2995-3000.

E. Favre, P. Schaetzel, Q.T. Nguygen, R. Clement, and J. Neel, Sorption, diffusion and vapor permeation of various penetrants through dense poly(dimethylsiloxane) membranes: a transport analysis, Journal of Membrane Science, 92, 1994, pp. 169-184.

J.M. Watson and M.G. Baron, The behaviour of water in poly(dimethylsiloxane), Journal of Membrane Science, 110, 1996, pp. 47-57.

Y. Tamai, H. Tanaka, and K. Nakanishi, Molecular Simulation of Permeation of Small Penetrants through Membranes, Macromolecules, 28, Nov. 7, 1995, pp. 2544-2554.

A. Kaplan, R. Jack, K.E. Opheim, B. Toivola, and A.W. Lyon, Clinical Chemistry: Interpretation and Techniques.

K. Annamalai and K.I. Puri, Advanced Thermodynamics Engineering; CRC Press, Washington, D.C., 2002, p. 673.

Y. Du, A.V. Mamishev, B.C. Lesieutre, M. Zahn, and S.H. Kang, Moisture Solubility for Differently Conditioned Transformer Oils, IEEE Transactions on Dielectrics and Electrical Insulation, vol. 8, No. 5, Oct. 2001, pp. 805-811.

Ismagilov, J.M.K. Ng, P.J.A. Kenis, and G.M. Whitesides, Microfluidic Arrays of Fluid—Fluid Diffusional Contacts as Detection Elements and Combinatorial Tools, Analytical Chemistry, Jul. 24, 2001, pp. A-G.

R.S. Suh, X. Zhu, N. Phadke, D.A. Ohl, S. Takayama, and G.D. Smith, IVF Within Microfluidic Channels Requires Lower Total Numbers and Lower Concentrations of Sperm, Human Reproduction, vol. 21, No. 2, Sep. 30, 2005, pp. 477-483, Oxford University Press on behalf of the European Society of Human Reproduction and Embryology.

K. Viravaidya, A. Sin, and M.L. Shuler, Development of a Microscale Cell Culture Analog to Probe Naphthalene Toxicity, Biotechnol. Prog., 2004, pp. 316-323, American Chemical Society and American Institute of Chemical Engineers.

E. Leclerc, Y. Sakai, and T. Fujii, Cell Culture in 3-Dimensional Microfluidic Structure of PDMS (polydimethylsiloxane), Biomedical Microdevices, 2003, pp. 109-114, Kluwer Academic Publishers, The Netherlands.

M.J. Powers, K. Domansky, M.R. Kaazembur-Mofrad, A. Kalezi, A. Capitano, A. Upadhyaya, P. Kurzawski, K.E. Wack, D.B. Stolz, R. Kamm, L.G. Griffith, A Microfabricated Array Bioreactor for Perfused 3D Liver Culture, Powers et al.; Microfabricated Array Bioreactor, 2002, cover page and pp. 257-269, Wiley Periodicals, Inc.

I.K. Glasgow, H.C. Zeringue, D.J. Beebe, S.-J. Choi, J.T. Lyman, N.G. Chan, and M.B. Wheeler, Handling Individual Mammalian Embryos Using Microfluidics, IEEE Transactions on Biomedical Engineering, vol. 48, No. 5, May 2001, pp. 570-577.

S.N. Bhatia, U.J. Balis, M.L. Yarmush, and M. Toner, Microfabrication of Hepatocyte/Fibroblast Co-cultures: Role of Homotypic Cell Interactions, Biotechnol. Prog. 14, May 20, 1998, pp. 378-387, American Chemical Society and American Institute of Chemical Engineers.

D. Beebe, M. Wheeler, H. Zeringue, E. Walters, and S. Raty, Microfluidic Technology for Assisted Reproduction, Theriogenology, 2002, cover page and pp. 126-135, 57, Elsevier Science Inc.

Song, W. Gu, N. Futai, K.A. Warner, J.E. Nor, and S. Takayama, Computer-Controlled Microcirculatory Support System for Endothelial Cell Culture and Shearing, Analytical Chemistry, vol. 77, No. 13, Jul. 1, 2005, pp. 3993-3999, American Chemical Society.

C.G. Koh, W. Tan, M.-Q. Zhao, A.J. Ricco, and Z.H. Fan, Integrating Polymerase Chain Reaction, Valving, and Electrophoresis in a Plastic Device for Bacterial Detection, Analytical Chemistry, vol. 75, No. 17, Sep. 1, 2003, pp. 4591-4598, American Chemical Society.

D.-S. Lee, S.H. Park, H. Yang, K.-H. Chung, T.H. Yoon, S.-J. Kim, K. Kim and Y.T. Kim, Bulk-micromachined submicroliter-volume PCR chip with very rapid thermal response and lower power consumption, Miniaturisation for Chemistry, Biology & Bioengineering, 2004, pp. 401-407, The Royal Society of Chemistry.

H.J. Crabtree, E.C.S. Cheong, D.A. Tilroe, and C.J. Backhouse, Microchip Injection and Separation Anomalies Due to Pressure Effects, Analytical Chemistry, vol. 73, No. 17, Sep. 1, 2001, pp. 4079-4086, American Chemical Society.

G.C. Randall and P.S. Doyle, Permeation-driven flow in poly(dimethylsiloxane) microfluidic devices, Proceedings of the National Academy of Sciences of the United States of America, vol. 102, No. 31, Aug. 2, 2005, pp. 10813-10818, The National Academy of Sciences of the USA.

C. Futterer, N. Minc, V. Bormuth, J.-H. Codarbox, P. Laval, J. Rossier, and J.-L. Viovy, Injection and flow control system for microchannels, Miniaturisation for Chemistry, Biology & Bioengineering, May 11, 2005, pp. 351-356, The Royal Society of Chemistry.

D.C. Duffy, H.L. Gillis, J. Lin, N.F. Sheppard, Jr., and G.J. Kellogg, Microfabricated Centrifugal Microfluidic Systems: Characterization and Multiple Enzymatic Assays, Analytical Chemistry, vol. 71, No. 20, Oct. 15, 1999, pp. 4669-4678, American Chemical Society.

P. Morier, C. Vollet, P.E. Michel, F. Reymond, J.S. Rossier, Gravity-induced convective flow in microfluidic systems: Electrochemical characterization and application to enzyme-linked immunosorbent assay tests, Electrophoresis, 2004, pp. 3761-3768, Wiley-VCH Verlag GmbH & Co.

S. Kanegasaki, Y. Nomura, N. Nitta, S. Akiyama, T. Tamatani, Y. Goshoh, T. Yoshida, T. Sato, Y. Kikuchi, A novel optical assay system for the quantitative measurement of chemotaxis, Journal of Immunological Methods, Jul. 22, 2003, pp. 1-11, Elsevier B.V.

G.B. Tennant, Stimulation of myeloid colony growth from peripheral blood by medium with an initially low osmolality, Int J Cell Cloning, Mar. 1990, 8(2), pp. 123-129.

\* cited by examiner

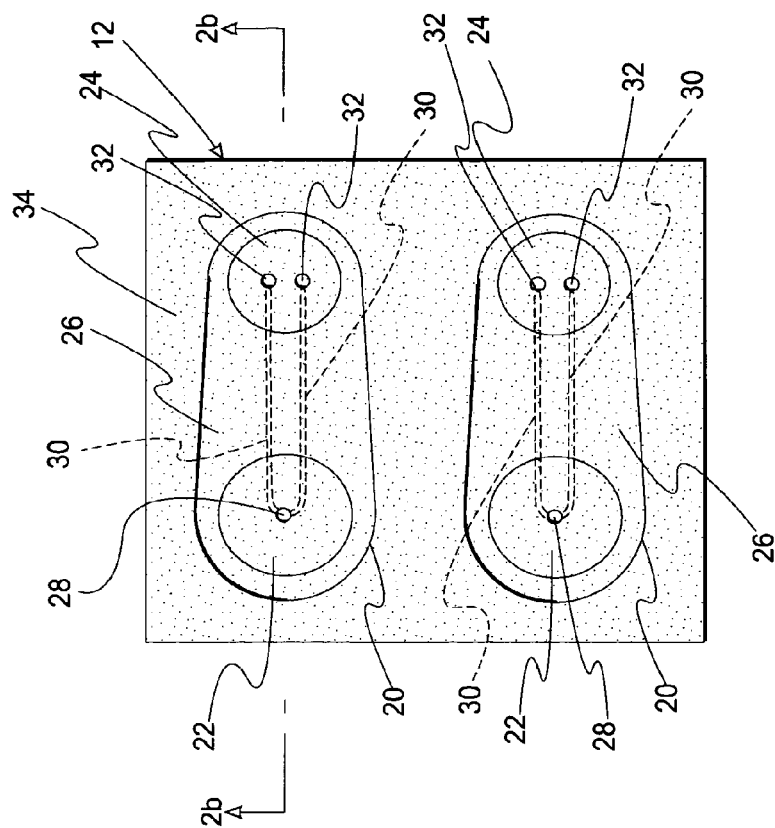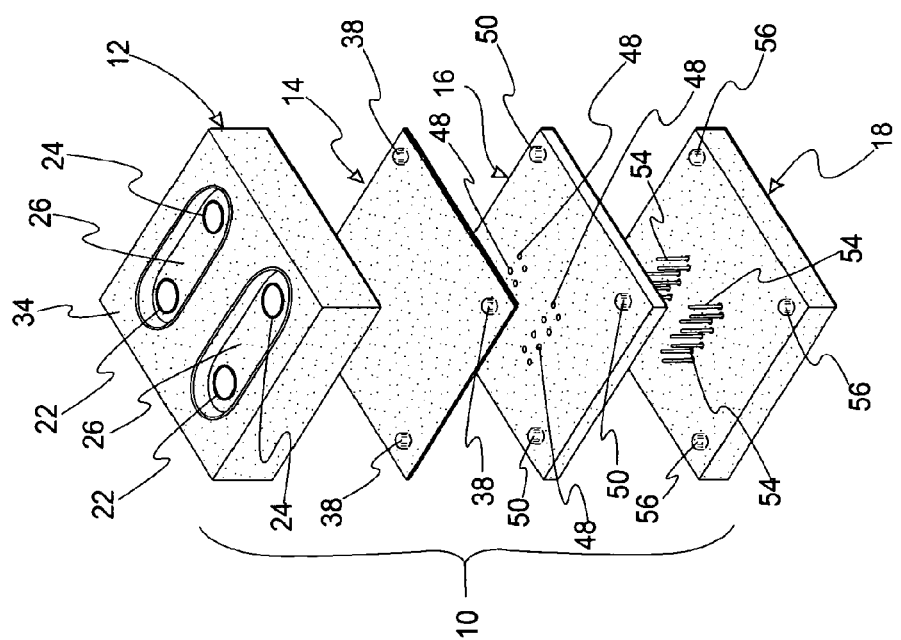

MICROFLUIDIC CELL CULTURE DEVICE

CROSS-REFERENCE TO RELATED APPLICATIONS

This application is a divisional of U.S. patent application 11/582,027, filed Oct. 17, 2006, now abandoned, which claims the benefit of the following U.S provisional applications Ser. No. 60/727,934 filed Oct. 18 2005 Ser. No. 60/728,030 filed Oct. 18, 2005 Ser. No. 60/741,665 filed Dec. 2, 2005 Ser. No. 60/741,864 filed Dec. 2, 2005 Ser. No. 60/802,705 filed May 23 2006 and Ser. No. 60/812,166 filed Jun. 9, 2006.

STATEMENT REGARDING FEDERALLY SPONSORED RESEARCH OR DEVELOPMENT

This invention was made with Government support under at least one of: Contract No. F012482; Contract No. F008090; Contract No. N006624; Grant No. HD049607-01 awarded by National Institute of Health; Contract/Grant No. DAAD19-03-1-0168 awarded by the U.S. Army Research Laboratory and the U.S. Army Research Office; BES-0238625 awarded by the National Science Foundation; NNC04AA21A awarded by the NASA BioScience and Engineering Institute; and USDA 2005-35203-16148 awarded by the United States Department of Agriculture. The Government has certain rights to the invention.

BACKGROUND

1. Field of the Invention

The invention relates to microfluidic cell culture devices.

2. Discussion

Microfluidic devices allow a user to work with nano- to microliter volumes of fluids and are useful for reducing reagent consumption, creating physiologic cell culture environments that better match the fluid-to-cell-volume ratios in vivo, and performing experiments that take advantage of low Reynolds number phenomenon such as subcellular treatment of cells with multiple laminar streams. Many microfluidic systems are made of polydimethylsiloxane (PDMS) because of its favorable mechanical properties, optical transparency, and bio-compatibility.

Cell culture is an essential tool in biological science, clinical science, and biotechnology. Microfluidic cell culture devices offer the advantages of increased fluid control, approximated physiologic culture environments, and improved culture efficiency.

Microfluidic cell culture devices have been developed for diverse cell types such as Eukaryotic cells, lung cells, embryonic stem cells, and mammalian embryos.

Most microfluidic cell culture devices separate cell loading zones from designated cell culture zones. This separation requires additional external forces and elaborate works for the cell in the loading zone to be transported to the designated culture zone. Also, the transport processes can put stress on sensitive cells such as mammalian embryo or embryonic stem cells. In addition, once the cells reach the designated culture zone, additional design and fabrications are required for cell confinement to apply diverse culture conditions with flows.

SUMMARY

Embodiments of the invention may take the form of a microfluidic cell culture device. The device includes a substrate and a reservoir formed in the substrate having upper and lower portions. The upper portion is sized to permit the insertion and removal of a cell mass from the reservoir. The device also includes a passage formed in the substrate and in fluid communication with the reservoir. At least one of the lower portion of the reservoir and the passage adjacent the lower portion is sized relative to the cell mass to retain at least a portion of the cell mass within the lower portion of the reservoir so that the cell mass can be directly removed from the lower portion through the upper portion.

The lower portion of the reservoir may be sized relative to the cell mass to retain at least a portion of the cell mass within the lower portion of the reservoir so that the cell mass can be directly removed from the lower portion through the upper portion.

The lower portion of the reservoir may have a width less than 250 micrometers to retain at least a portion of the cell mass within the reservoir.

The lower portion of the reservoir may have a width, the cell mass may be a denuded human zygote, and the width may be less than 140 micrometers to retain at least a portion of the cell mass within the reservoir.

The lower portion of the reservoir may have a width, the cell mass may be a denuded mammalian zygote, and the width may be less than 70 micrometers to retain at least a portion of the cell mass within the reservoir.

The lower portion of the reservoir may have a width, the cell mass may be a clump of mammalian cells, and the width may be less than 50 micrometers to retain at least a portion of the cell mass within the reservoir.

The lower portion of the reservoir may have a width, the cell mass may be a single mammalian cell, and the width may be less than 5 micrometers to retain at least a portion of the cell mass within the reservoir.

The passage adjacent the lower portion may be sized relative to the cell mass to retain at least a portion of the cell mass within the lower portion of the reservoir so that the cell mass can be directly removed from the lower portion through the upper portion.

The passage adjacent the lower portion may have a passage width and a passage height and at least one of the passage height and the passage width may be less than 250 micrometers to retain at least a portion of the cell mass within the reservoir.

The passage adjacent the lower portion may have a passage width and a passage height, the cell mass may be a denuded human zygote, and at least one of the passage height and the passage width may be less than 140 micrometers to retain at least a portion of the cell mass within the reservoir.

The passage adjacent the lower portion may have a passage width and a passage height, the cell mass may be a denuded mammalian zygote, and at least one of the passage height and the passage width may be less than 70 micrometers to retain at least a portion of the cell mass within the reservoir.

The passage adjacent the lower portion may have a passage width and a passage height, the cell mass may be a clump of mammalian cells, and at least one of the passage height and the passage width may be less than 50 micrometers to retain at least a portion of the cell mass within the reservoir.

The passage adjacent the lower portion may have a passage width and a passage height, the cell mass may be a single mammalian cell, and at least one of the passage height and the passage width may be less than 5 micrometers to retain at least a portion of the cell mass within the reservoir.

A cross-section of the reservoir may have a polygonal shape. The reservoir may have a frusta-conical shape.

An angle defined by opposite surfaces of the reservoir may be between 30 degrees and 160 degrees inclusive.

The upper portion may have an upper width and the lower portion may have a lower width and the upper width may be greater than the lower width.

A surface of the reservoir may taper inwardly from the upper portion to the lower portion.

The passage may be U-shaped.

The passage may have a volume less than 1 microliter.

While exemplary embodiments in accordance with the invention are illustrated and disclosed, such disclosure should not be construed to limit the claims. It is anticipated that various modifications and alternative designs may be made without departing from the scope of the invention.

BRIEF DESCRIPTION OF THE DRAWINGS

FIG. 1 is an exploded, perspective view of a microfluidic cell culture device in accordance with an embodiment of the invention;

FIG. 2a is a top view of a substrate of the system of FIG. 1;

FIG. 2b is a side view, and in cross-section, of the substrate taken along section line 2b-2b in FIG. 2a;

FIG. 2c is a bottom view of the substrate of FIG. 2a;

DETAILED DESCRIPTION

Figure 2B:
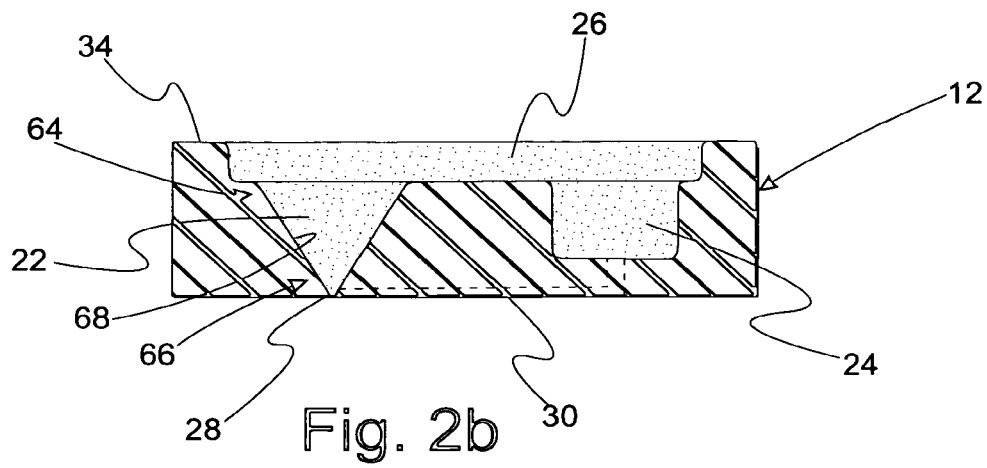

FIG. 1 is an exploded, perspective view of microfluidic cell culture system or device 10. Device 10 includes substrate 12 configured to receive a cellular mass, e.g., an embryo, as explained in detail below, non-rigid membrane 14, locating block 16, and pin actuating device 18.

FIG. 2a is a top view of substrate 12. Substrate 12 includes funnel 22, reservoir 24, and overlay reservoir 26. Bottom portion 28 of funnel 22 is in fluid communication with reservoir 24 via microchannel 30. Microchannel 30 has a volume less than 1 microliter. Reservoir 24 includes reservoir openings 32 which provide openings to microchannel 30 such that fluids may travel between funnel 22 and reservoir 24 as explained in detail below.

FIG. 2b is a side view, and in cross-section, of substrate 12 taken along section line 2b-2b in FIG. 2a. A portion of microchannel 30 is formed in substrate 12 while another portion of microchannel 30 is formed by membrane 14 as described in detail below. Microchannel 30, however, may be completely formed in substrate 12 or in any other suitable fashion. Microchannel 30 may have a square, circular, bell, or any other suitably shaped cross-section. Substrate 12 further includes hydrophilic surface 34 to promote fluid retention within overlay reservoir 26.

Fluid may move between funnel 22 and reservoir 24 via localized deformation of membrane 14. Fluid may also move between funnel 22 and reservoir 24 under the influence of gravity as explained in detail below.

Substrate 12 may be optically transparent and made from such materials as plastic, e.g., PDMS, polymethylmethacrylate, polyurethane, or glass.

Figure 2C:
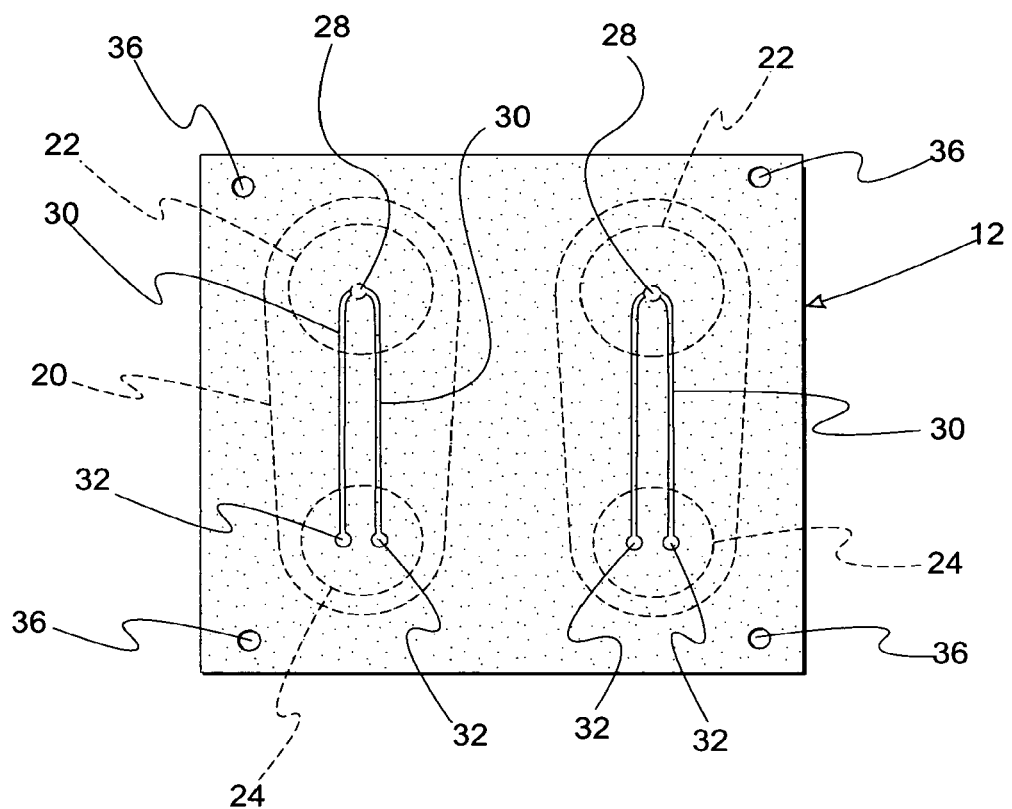

FIG. 2c is a bottom view of substrate 12. Substrate 12 includes female locators 36 which assist in locating substrate 12 relative to membrane 14 as explained in detail below.

Substrate 12 may comprise a thick, e.g., 8 mm, PDMS slab, fabricated by using soft lithography. The PDMS slab may be prepared by casting a prepolymer (Sylgard 184, Dow-Corning) at a 1:10 curing agent-to-base ratio against positive relief features. Relief features may comprise SU-8 (MicroChem, Newton, Mass.) and be fabricated on a thin, e.g., 200 µm, glass wafer by using backside diffused-light photolithography. The prepolymer may then cure at 60° C. for 60 minutes, and holes may be punched by a sharpened 14-gauge blunt needle.

Substrate 12 may comprise two layers of cured PDMS at a ratio of 1:10 base to curing agent sealed together irreversibly using plasma oxidation (SPI supplies, West Chester, Pa.). Funnel 22 and reservoir 24 are formed in the top layer. Microchannel 30 is formed in the bottom layer using soft lithography. Microchannel 30 faces downward and may be sealed against membrane 14 as explained in detail below.

Figure 3A:
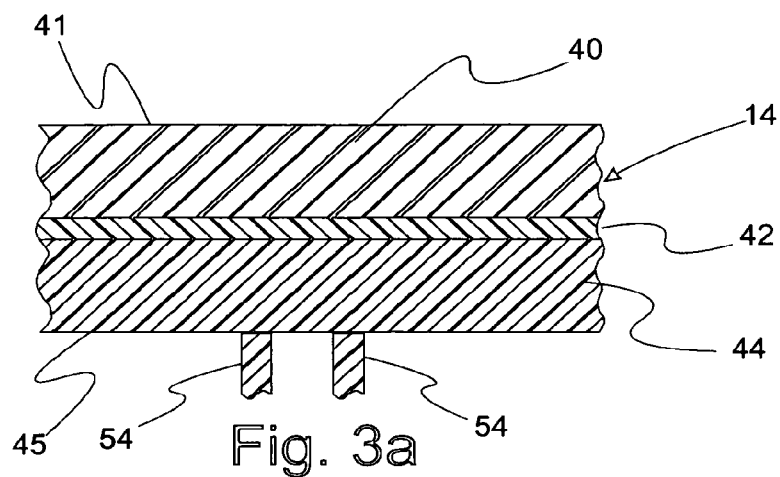
FIG. 3a is a side view, partially broken-away and in cross-section, of a membrane of the system of FIG. 1 with a pair of actuator pins in engagement with a lower surface of the membrane.

FIG. 3a is a side view, partially broken-away and in cross-section, of membrane 14 and pins 54 of pin actuating device 18 (FIG. 1). Membrane 14 includes male locators 38 (FIG. 1) configured to be received by female locators 36 of substrate 12 to locate membrane 14 relative to substrate 12.

Membrane 14 is optically transparent and includes top layer 40, upper surface 41, middle layer 42, bottom layer 44, and bottom surface 45. Top layer 40 and bottom layer 42 comprise PDMS. Middle layer 42 comprises parylene. Top layer 40 and bottom layer 44, alternatively, may comprise any suitable non-rigid, bio-compatible polymer such as a non-rigid plastic, e.g., polyurethane, or a hyrdrogel, e.g., polyvinylalcohol. Middle layer 42, alternatively, may comprise any suitable non-rigid polymer such as polyvinylidene chloride or polyurethane.

Top layer 40 and bottom layer 44 may have a combined thickness of less than 1 mm, e.g., 200 µm. Middle layer 42 may range in thickness from 2-20 µm, e.g., 2-5 µm.

Pins 54 of pin actuating device 18 may selectively extend from the position shown into membrane 14 to locally deform membrane 14 such that at least a portion of top layer 40 extends into microchannel 30 (FIG. 2b). The selective actuation of pins 54 may move a fluid in microchannel 30 or prevent, or impede, the movement of the fluid in microchannel 30 as explained in detail below.

Middle layer 42 minimizes evaporation of a fluid, e.g., a water based fluid, contained within microchannel 30 to prevent, for example, undesirable shifts in osmolality of the fluid. Middle layer 42 is also resistant to the flow of at least one gas, such as oxygen and carbon dioxide, from microchannel 30 and provides mechanical durability and stability against cracking caused by the selective actuation of pins 54. Fatigue from the actuation of pins 54 does not substantially increase middle layer's 42 ability to substantially reduce the rate at which a fluid from microchannel 30 moves through membrane 14.

Membrane 14 includes female locators (not shown) which are used to locate membrane 14 relative to locating block 16 as explained in detail below.

Membrane 14 may be prepared by spin-coating PDMS onto a 4" silanized silicon wafer to a thickness of 100 µm, curing this layer at 120° C. for 30 minutes, depositing a 2.5 or 5 µm thick parylene layer, plasma oxidizing the resulting parylene surface for 90 seconds, spin-coating another 100 µm thick layer of PDMS, and curing for a total thickness of approximately 200 µm.

Figure 3B:
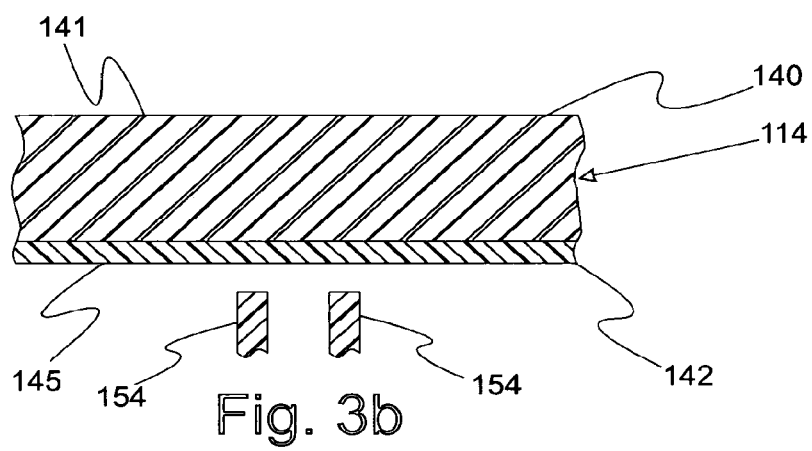
FIG. 3b is a side view, partially broken-away and in cross-section, of an alternative embodiment of a membrane of the system of FIG. 1 with a pair of actuator pins spaced away from the lower surface of the membrane.

FIG. 3b is a side view, partially broken-away and in cross-section, of an alternative embodiment of membrane 114 and pins 154 of pin actuating device 118 (not shown). Membrane 114 includes top layer 140, upper surface 141, bottom layer 142, and lower surface 145. Top layer 140 comprises PDMS and bottom layer 142 comprises polyvinylidene chloride. Top layer 140, alternatively, may comprise any suitable non-rigid, bio-compatible polymer such as a non-rigid plastic, e.g., polyurethane, or a hyrdrogel, e.g., polyvinylalcohol, whereas bottom layer 142 may comprise any suitable non-rigid polymer such as polyurethane.

Top layer 140 and bottom layer 142 may have a combined thickness of less than 1 mm, e.g., 200 µm.

Bottom layer 142 minimizes evaporation of a fluid, e.g., a water based fluid, contained within microchannel 30 to prevent, for example, undesirable shifts in osmolality of the fluid. Bottom layer 142 is also resistant to the flow of at least one gas, such as oxygen and carbon dioxide, from microchannel 30 and provides mechanical durability and stability against cracking caused by the selective actuation of pins 154. Fatigue from the actuation of pins 154 does not substantially increase bottom layer's 142 ability to substantially reduce the rate at which a fluid from microchannel 30 moves through membrane 114.

Membrane 114 may be prepared by spin-coating freshly mixed 1:10 PDMS onto silanized glass slides (Corning Glass Works, Corning, N.Y.) to a uniform thickness of either approximately 120 µm or 400 µm, curing overnight at 120° C., and then adhering polyvinylidene chloride via conformal contact with the PDMS.

Referring to FIG. 1, locating block 16 includes pin holes 48 and male locators 50. Pin holes 48 are configured to receive pins 54 of pin actuating device 18. Male locators 50 are configured to be received by the female locators of membrane 14 to locate locating block 16 relative to membrane 14. In particular, by locating block 16 relative to membrane 14, pin holes 48 are aligned with microchannel 30. Locating block 16 includes female locators (not shown) which are used to locate locating block 16 relative to pin actuating device 18 as explained in detail below.

Locating block 16 is rigid and optically transparent and made from such materials as polystyrene, cyclic olefin copolymer, glass, or metal.

Pin actuating device 18 is a Braille-type actuator as described in detail below. Pins 54 are actuated with a force of 18 g. Pins 54, however, may be actuated with a force ranging from approximate 3 g to 300 g. Pins 54 may be actuated, for example, 10 times per second or once a minute. Pins 54 may be actuated for a period ranging from minutes to weeks. Any suitable tactile device, however, may be used.

Pins 54 of pin actuating device 18, when actuated, extend and press upon membrane 14, restricting or closing microchannel 30. Pins 54 may be actuated in any suitable fashion such that a fluid flows between funnel 22 and reservoir 24 via microchannel 30. Pins 54 may also be actuated such that the fluid does not move between funnel 22 and reservoir 24 via microchannel 30.

Pin actuating device 18 includes male locators 56. Male locators 56 are configured to be received by female locators 52 of locating block 16 to align locating block 16 relative to pin actuating device 18. By aligning locators 46, 56, pins 54 are aligned with pin holes 48.

Figure 4A:
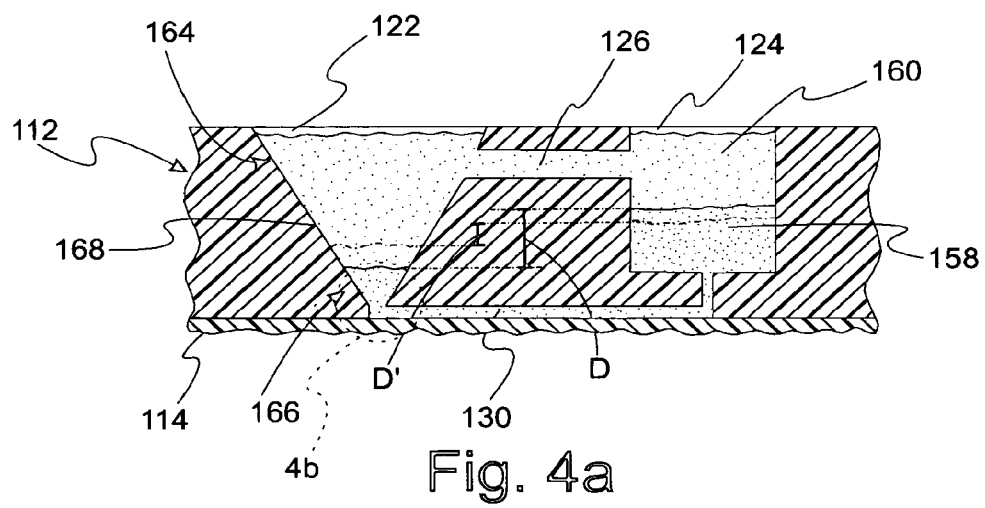
FIG. 4a is a side view, partially broken-away and in cross-section, of an alternative embodiment of the substrate of FIG. 1 and the membrane of FIG. 3b and illustrating two different heights of a biological fluid in a pair of reservoirs formed in the substrate.

FIG. 4a is side view, partially broken-away and in cross-section, of substrate 112 and membrane 114. Reservoir 124 and funnel 122 are in fluid communication via microchannel 130. Bio-compatible fluid 158 may be transported between reservoir 124 and funnel 122 via localized deformation of membrane 114 by pin actuating device 118. D is the difference in height between bio-compatible fluid 158 in reservoir 124 and funnel 122.

Funnel 122 and reservoir 124 are further in fluid communication via upper channel 126. Microchannel 130 has a resistance to fluid flow greater than upper channel 126. Upper channel 126 is defined by a hydrophobic surface to, for example, repel bio-compatible fluid 158.

Immiscible fluid 160, e.g., an oil having a density lower than bio-compatible fluid 158, may move between funnel 122 and reservoir 124 via channel 126. Immiscible fluid 160 reduces evaporation of bio-compatible fluid 158 and reduces the flow of oxygen and carbon dioxide into and out bio-compatible fluid 158. Gravity will act upon immiscible fluid 160 such that the height of immiscible fluid 160 in funnel 122 will equal the height of immiscible fluid 160 in reservoir 124 thereby maintaining the difference in height, D, of bio-compatible fluid 158.

D' is the desired difference in height between bio-compatible fluid 158 in funnel 122 and bio-compatible fluid 158 in reservoir 124 after pin actuating device 118, for example, has been used to move bio-compatible fluid 158 from reservoir 124 to funnel 122. Such a height may provide a desired amount of fluid in funnel 122 conducive to cell culturing. As bio-compatible fluid 158 is moved from reservoir 124 to funnel 122, immiscible fluid 160 will flow from funnel 122 to reservoir 124 via channel 126 under the influence of gravity such that in the absence of deformation of membrane 114 that would cause, for example, bio-compatible fluid 158 to further move between funnel 122 and reservoir 124 or prevent bio-compatible fluid 158 from moving between funnel 122 and reservoir 124, immiscible fluid 160 will substantially maintain the difference in height D' under the influence of gravity for a desired period of time, e.g., approximately 30 minutes. Microchannel 130 and channel 126 thus from a continuous fluid path between funnel 122 and reservoir 124.

Fluid may move between funnel 122 and reservoir 124 in any number of ways. For example, a pump may pump immiscible fluid 160 from one of funnel 122 and reservoir 124 to the other of funnel 122 and reservoir 124 thereby changing the height of bio-compatible fluid 158.

Funnel 122 includes upper portion 164 and lower portion 166. Surface 168 of funnel 122 tapers inwardly from upper portion 164 to lower portion 166. Furthermore, upper portion 164 has a width greater than lower portion 166.

The shape of funnel 122 facilities the one-step loading and unloading of cells into and out of lower portion 166. A pipette holding cells may be inserted into funnel 122 at an angle such that a user has a substantially unobstructed view of lower portion 166. Likewise, a pipette may be inserted into funnel 122 to remove cells from lower portion 166 such that a user has a substantially unobstructed view of lower portion 166.

Figure 4B:
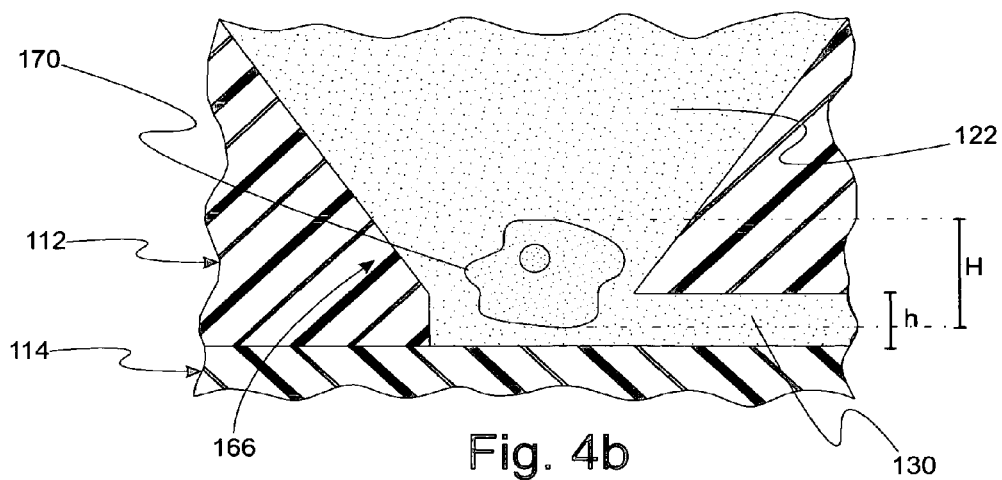
FIG. 4b is an enlarged side view, partially broken-away and in cross-section, of the substrate and membrane of FIG. 4a and illustrating the relative heights of a cell mass and an end portion of a passageway.

FIG. 4b is an enlarged side view, partially broken-away and in cross-section, of funnel 122 and microchannel 130. Lower portion 166 of funnel 122 is configured to receive cellular mass 170. Cellular mass 170 has a cellular height H and microchannel 130 has a channel height h. Cellular mass 170 may be, for example, a human zygote, a mammalian zygote, a clump of mammalian cells, or a single mammalian cell. Microchannel 130 is configured such that cellular mass 170 will not exit lower portion 166 of funnel 122.

Figure 4C:
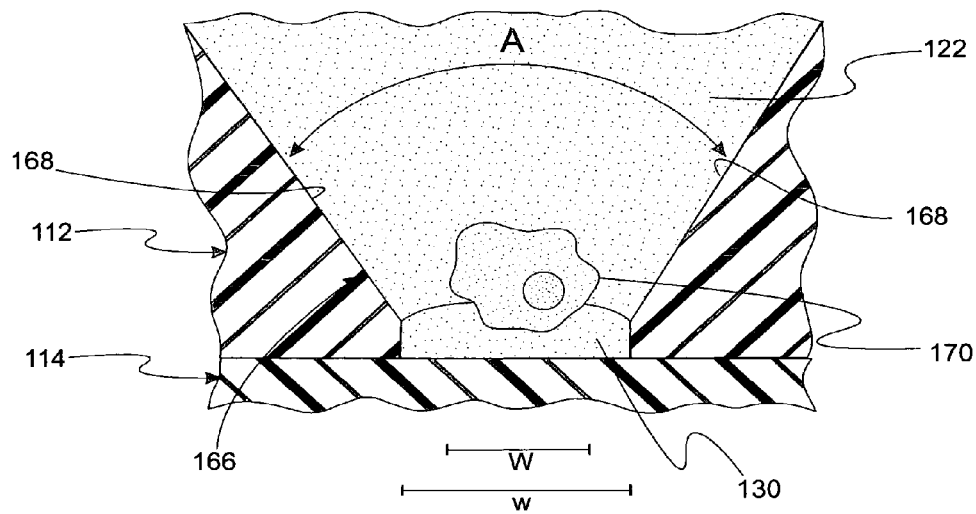
FIG. 4c is another enlarged side view, partially broken-away and in cross-section, of the substrate and membrane of FIG. 4a and illustrating the angle of the surface which defines a reservoir and the relative widths of a cell mass and a lower portion of the reservoir.

FIG. 4c is another enlarged side view, partially broken-away and in cross-section, of funnel 122 and microchannel 130 looking down the length of microchannel 130. Cellular mass 170 has a cellular width W and microchannel 130 has a channel width w. Cellular mass 170 also has a cellular length (not shown). Microchannel 130 may be configured such that at least one of the channel height h and the channel width w is less than at least one of the cellular height H, the cellular width W, and the cellular length L.

Angle A is defined by opposite surfaces 168 of funnel 122. Angle A may range between 30° and 160° inclusive.

At least one of the channel height h and the channel width w may be less than 250 μm or the width of human hair. In the case where cellular mass 170 is a denuded human zygote, at least one of the channel height h and the channel width w may be less than 140 μm. In the case where cellular mass 170 is a denuded mammalian zygote, at least one of the channel height h and the channel width w may be less than 70 μm. In the case where cellular mass 170 is a clump of mammalian cells, at least one of the channel height h and the channel width w may be less than 50 μm. In the case where cellular mass 170 is a single mammalian cell, at least one of the channel height h and the channel width w may be less than 5 μm.

Figure 5A:
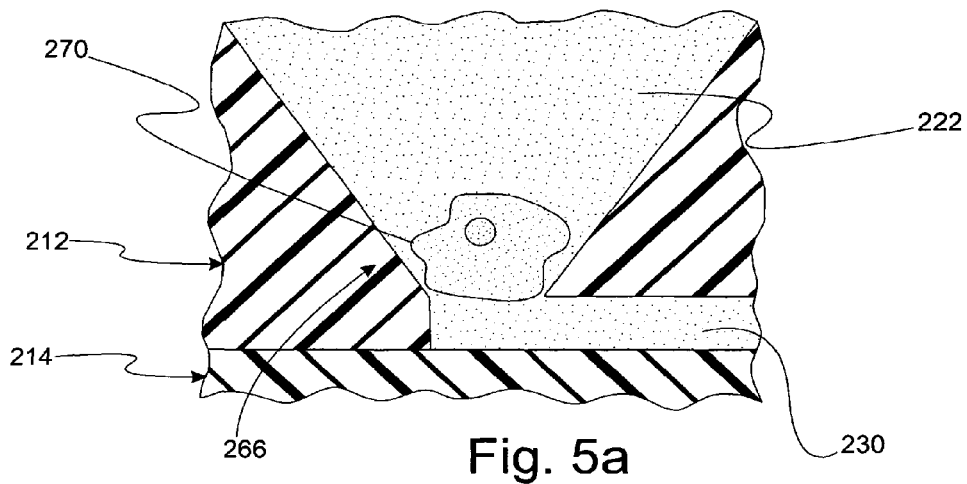
FIG. 5a is an enlarged side view, partially broken-away and in cross-section, of an alternative embodiment of a substrate and membrane of FIG. 1 and illustrating a cell mass retained in a lower portion of the reservoir above the passageway.

FIG. 5a is an enlarged side view, partially broken-away and in cross-section, of funnel 222 and microchannel 230. Lower portion 266 is sized such that a portion of cellular mass 270 is confined to lower portion 266.

Lower portion 266 may have a width less than 250 μm. In the case where cellular mass 270 is a denuded human zygote, the width may be less than 140 μm. In the case where cellular mass 270 is a denuded mammalian zygote, the width may be less than 70 μm. In the case where cellular mass 270 is a clump of mammalian cells, the width may be less than 50 μm. In the case where cellular mass 270 is a single mammalian cell, the width may be less than 5 μm.

Figure 5B:
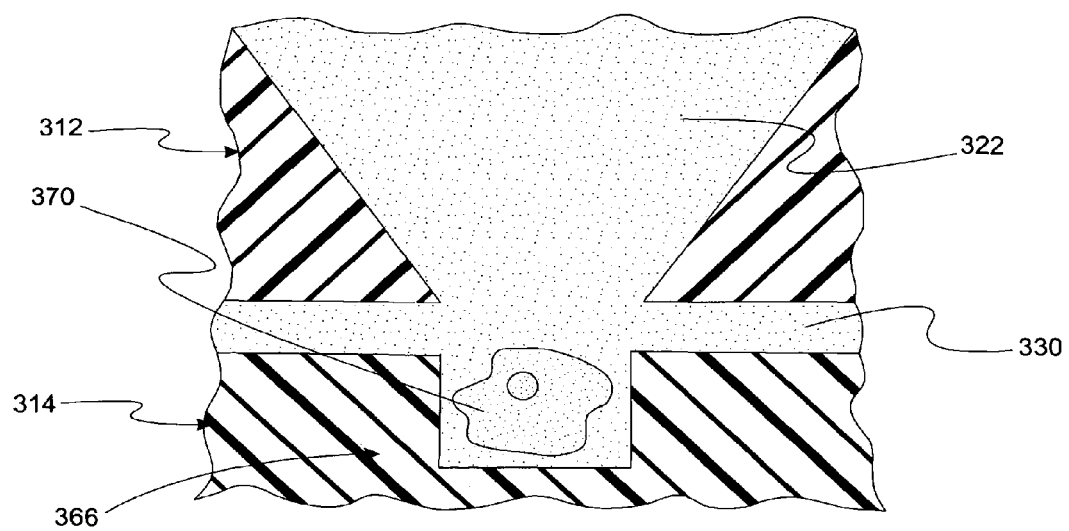
FIG. 5b is another enlarged side view, partially broken-away and in cross-section, of an alternative embodiment of a substrate and membrane of FIG. 1 and illustrating a cell mass retained in a lower portion of the reservoir below the passageway.

FIG. 5b is an enlarged side view, partially broken-away and in cross-section, of funnel 322 and microchannel 330. Lower portion 366 is sized such that a portion of cellular mass 370 is confined to lower portion 366. Additionally, microchannel 330 is above lower portion 366.

Figure 5C:
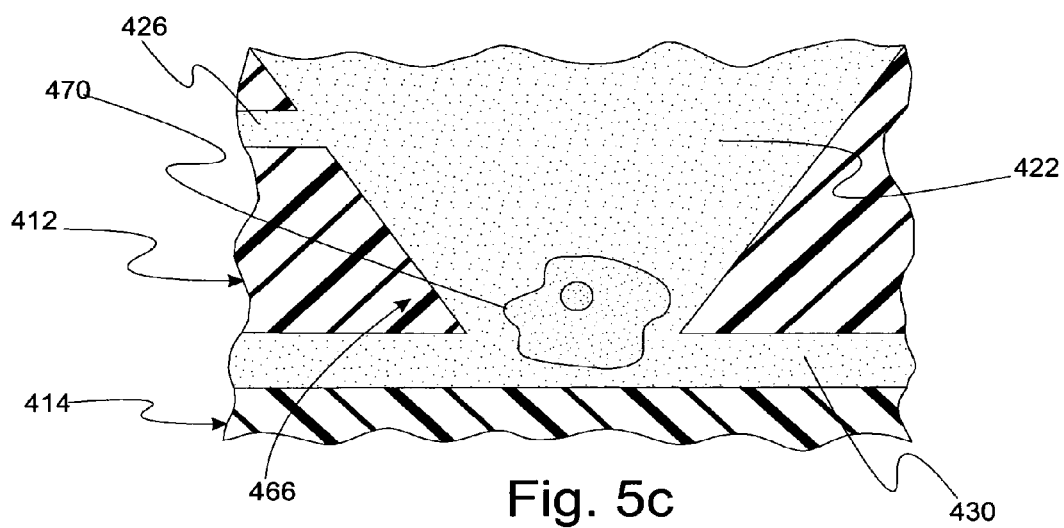
FIG. 5c is yet another enlarged side view, partially broken-away and in cross-section, of an alternative embodiment of a substrate and membrane of FIG. 1 and illustrating a cell mass with a width smaller than the width of the lower portion of the reservoir.

FIG. 5c is an enlarged side view, partially broken-away and in cross-section, of funnel 422 and microchannel 430. Lower portion 466 and microchannel 430 are sized such that portions of cellular mass 470 may be in either of lower portion 466 and the portion of microchannel 430 adjacent lower portion 466.

Embodiments of the invention may take the form of a microfluidic device composed of a PDMS slab with bell-shaped microfluidic channel features, a culture media reservoir, and a funnel shaped well for culture. The media reservoir and funnel shaped well are connected with the microfluidic channels. The funnel shaped well may have an approach angle of approximately 60° to facilitate the one-step loading and unloading of cells and an approximately 500 μm diameter tip.

In funnel type wells, cells do not need to be moved to designated areas. Instead, cells loaded in the funnel remain stationary. The medium or chemical composition in the funnel can be gradually changed to mimic conditions cells experience in vivo. In addition, the dimensions of the channels connected to the funnel can be controlled through soft-lithography processes such that cells are confined to the funnel. Cells may then be subjected to diverse flow conditions.

PDMS slabs may be prepared by casting prepolymer (Sylgard 184, Dow-Corning) at a 1:10 curing agent-to-base ratio against positive relief features approximately 30 μm in height and 400 μm in width. The relief features may comprise SU-8 (MicroChem, Newton, Mass.) and be fabricated on a thin glass wafer, approximately 200 μm thick, using backside diffused-light photolithography.

Embodiments of the invention may include a tapered well which at its tip has an opening which communicates with one or a plurality of microchannels. The well and microchannels may be filled with fluid. One or more cells, e.g., embryos, may be introduced into the well, for example, by pipet. The cells settle to the bottom, but are prevented from exiting the well due to them being larger than the microchannels.

Fluid may be introduced into the well continuously or discontinuously. The fluid may contain the necessary growth media for the cells. In a well with a single hole at the bottom, for example, fluid may be caused to rise in the well from the microchannels, introducing extra nutrients, and then to fall, removing fluid which now contains exogenous substances, e.g., waste, via the microchannels.

Introduction and removal of fluid can be made using conventional gravity pumps or constant flow gravity driven pumps. Introduction and removal of fluid can also be made by outside supplies, such as pumps, or by on-board or "semi-on-board" tactile actuator-based pumping systems.

Wells may have inlets at other locations and or heights rather than at the bottom, so long as the entrance ways are sized such that cells will not pass into the channels. For example, there may be an opening at the bottom of a well and an opening near the middle or top, with fluid being supplied at the bottom and being removed closer to the top.

Wells may have a polygonal shape whose walls are inclined, in either a linear or curved fashion, such that cells added to the well have a tendency to gravitate toward the bottom and center of the well.

The material in which a well is formed may be, for example, thermosetting resin, thermoplastic, metal, glass, or ceramic.

Embodiments of the invention may take the form of a multilayer device. The top layer containing a well, and constructed of a relatively rigid material so as to provide support for elastomeric layers or layers of lesser strength or modulus below. The top layer may comprise a hard transparent material, such as glass or polymethylmethacrylate. The well may have a low surface roughness ranging, for example, between 5 μm Ra and 0.1 μm Ra.

The well may penetrate through the top layer, thus having an open, wide-mouthed end on one side of the top layer, and on the bottom layer, a relatively narrow hole which allows fluid communication with microchannels in the second layer.

The microchannels may be positioned closely with respect to the opening in the well to minimize misalignment. For example, misalignment should not exceed 50 μm. The second layer may also constitute the bottom layer, particularly when the microchannels are substantially on top of the second layer, e.g, abutting the bottom surface of the top layer.

Embodiments of the invention may include microchannels that are, at least in part, along the bottom of the second layer. A third, or sealing layer may be applied thereto. This sealing layer may be rather thin, such that braille-type tactile actuators may act as valves and pumps for the various microchannels. By this means, for example, fluid can be caused to flow or to be pumped in one or both directions in a given microchannel depending upon the valving, whether the valves are on or off, and whether a pump is pumping one way or the other with respect to the microchannel.

In use, a well is first filled with fluid, e.g., an embryo culture medium, and one or more embryos added to the well. An oil overlay, produced by dropping one or two fine drops of oil onto the liquid surface in the well, is then provided.

The oil prevents evaporation of liquid from the well, thus stabilizing the osmolality, or concentration, of the ingredients therein. The oil overlay also affects the flow of air, including specifically oxygen and $CO_2$ into the fluid, and the release of these gases from the fluid. The oil may be any compatible oil, for example, a silicone oil, a paraffin oil, or a polyethylene oligomer oil. For the same reason, the second or third layers, if present, may include, for example, parylene, or other materials, which minimize water loss.

The second and third layers may be made of cast elastomer, particularly when the embodiments employ tactile actuators. If "off-chip" fluid supply or valving is used, however, the use of an elastomer is not necessary, and other materials, such as cast epoxy, injection molded thermoplastic, or glass, can be used. The surface of these materials should be bio-compatible, and if not, should be coated appropriately.

Zygotes may be introduced into a well containing a fluid as is conventionally employed for embryo culture. The fluid in the well is then covered with oil and incubated at a suitable temperature. Fluid is directed into and out of the well through microchannels continuously or discontinuously, e.g., a back and forth type of fluid supply wherein the fluid level in the well increases and then decreases cyclically. The growing embryo may be inspected by conventional optical microscopy methods, and when judged grown to the proper stage, the embryo is removed from the well. If the top of the well is larger then the bottom, one-step removal is particularly easy and the risk of damage to the embryo is low.

Embodiments of the invention may contain microchannels whose flow characteristics are to be actively varied and formed in a compressible or distortable elastomeric material such as an organopolysiloxane elastomer. Substrates, however, may be constructed of hard, e.g., substantially non-elastic material at portions where active control is not desired.

Embodiments of the invention may contain at least one active portion which alters the shape or volume of chambers or passageways ("empty space"). Such active portions include mixing portions, pumping portions, valving portions, flow portions, channel or reservoir selection portions, cell crushing portions, and unclogging portions. These active portions induce some change in the fluid flow, fluid characteristics, channel, or reservoir characteristics by exerting a pressure on the relevant portions of the microfluidic device, and thus alter the shape or volume of the empty space which constitutes these features. The term "empty space" refers to the absence of substrate material. In use, the empty space may be filled with fluid.

The active portions may be activatable by pressure to close their respective channels or to restrict the cross-sectional area of the channels to accomplish the desired active control. To achieve this purpose, the channels or reservoirs may be constructed in such a way that modest pressure from the exterior of the microfluidic device causes the channels or reservoirs ("microfluidic features") to compress, causing local restriction or total closure of the respective feature.

Walls surrounding the feature and external surfaces may be elastomeric such that a minor amount of pressure causes an external surface and, optionally, the internal feature walls to distort, either reducing cross-sectional area at this point or completely closing the feature.

The pressure required to "activate" the active portion(s) of the device may be supplied by an external tactile device such as a refreshable Braille display. The tactile actuator contacts the active portion of the device, and when energized, extends and presses upon the deformable elastomer, restricting or closing the feature in the active portion.

Dimensions of the various flow channels and reservoirs may be determined by volume and flow rate properties. Channels which are designed for complete closure may be of a depth such that the elastomeric layer between the microchannel and the actuator can approach the bottom of the channel. Manufacturing the substrate of elastomeric material facilitates complete closure, in general, as does also a cross-section which is rounded, particularly at the furthest corners (further from the actuator). The depth will also depend, for example, on the extension possible for the actuator's extendable protrusions, e.g., pins. Thus, channel depths may vary, for example, from 1 nm to 500 μm.

Embodiments of the invention may be prepared through the use of a negative photoresist, for example, SU-8 50 photoresist (Micro Chem. Corp., Newton, Mass.) The photoresist may be applied to a glass substrate and exposed from the uncoated side through a suitable mask. Since the depth of cure is dependant on factors such as length of exposure and intensity of the light source, features ranging from very thin up to the depth of the photoresist may be created. The unexposed resist is removed, leaving a raised pattern on the glass substrate. The curable elastomer is cast onto this master and then removed.

The material properties of SU-8 photoresist and the diffuse light from an inexpensive light source can be employed to generate microstructures and channels with cross-sectional profiles that are rounded and smooth at the edges yet flat at the top, e.g, bell-shaped. Short exposures tend to produce a radiused top, while longer exposures tend to produce a flat top with rounded corners. Longer exposures also tend to produce wider channels. These profiles are ideal for use as compressive, deformation-based valves that require complete collapse of the channel structure to stop fluid flow. With such channels, Braille-type actuators produce full closure of the microchannels, thus producing a very useful valved microchannel. Such shapes also lend themselves to produce uniform flow fields, and have good optical properties as well.

In a typical procedure, a photoresist layer is exposed from the backside of the substrate through a mask, for example photoplotted film, by diffused light generated with an ultraviolet (UV) transilluminator. Bell-shaped cross-sections are generated due to the way in which the spherical wavefront created by diffused light penetrates into the negative photoresist. The exposure dose dependent change in the SU-8 absorption coefficient limits exposure depth at the edges.

The exact cross-sectional shapes and widths of the fabricated structures may be determined by a combination of photomask feature size, exposure time/intensity, resist thickness, and distance between the photomask and photoresist. Although backside exposure makes features which are wider than the size defined by the photomask and in some cases smaller in height compared to the thickness of the original photoresist coating, the change in dimensions of the transferred patterns is readily predicted from mask dimensions and exposure time.

The relationship between the width of the photomask patterns and the photoresist patterns obtained is essentially linear, e.g., slope of 1, beyond a certain photomask aperture size. This linear relationship allows straightforward compensation of the aperture size on the photomask through simple subtraction of a constant value. When exposure time is held constant, there is a threshold aperture size below which incomplete exposure will cause the microchannel height to be lower than the original photoresist thickness. Lower exposure doses will make channels with smoother and more rounded cross-sectional profiles. Light exposure doses that are too slow or photoresist thicknesses that are too large, however, are insufficient in penetrating through the photoresist, resulting in cross-sections that are thinner than the thickness of the original photoresist.

The suitability of bell-shaped cross-section microchannels of 30 µm thickness may be evaluated by exerting an external force onto the channel using a piezoelectric vertical actuator of commercially available refreshable Braille display. Spaces may be left between the membrane and the wall when the channel cross-section has discontinuous tangents, such as in rectangular cross-sections. In contrast, a channel with a bell-shaped cross-section may be fully closed under the same conditions. When a Braille pin is pushed against a bell-shaped or rectangular-shaped cross-section microchannel through a 200 µm PDMS membrane, the bell-shaped channels may be fully closed while the rectangular channels of the same width may have considerable leakage.

When used as deformation-based microfluidic valves, bell-shaped microchannels may show self-sealing upon compression compared to conventional rectangular or semi-circular cross-section channels. By way of example, a bell-shaped channel, having a width and height of 30 µm, may be completely closed by an 18 gf-force squeeze of a Braille pin.

Channels that have the bell-shaped cross-sections with gently sloping sidewalls may not be fabricated by melting resist technology, one of the most convenient methods to fabricate photomask-definable rounded patterns, because the profile is determined by surface tension.

Bell-shaped channels maximize the cross-sectional area within microfluidic channels without compromising the ability to completely close channels upon deformation. Furthermore, bell-shaped cross-sections provide channels with flat ceilings and floors, which is advantageous for reducing aberrations in optical microscopy and in obtaining flow fields with a more uniform velocity profile across the widths of the channel. These advantages of microchannels with bell-shaped cross-sectional shapes combined with the convenient, inexpensive, and commercially available valve actuation mechanism based on refreshable Braille displays will be useful for a wide range of microfluidic applications such as microfluidic cell culture and analysis systems, biosensors, and on-chip optical devices such as microlenses.

The extension outwards of tactile actuators should be sufficient for their desired purpose. Complete closure of a 40 µm deep microchannel, for example, will generally require a 40 µm extension, e.g., pin, or more when a single actuator is used, and about 20 µm or more when dual actuators on opposite sides of the channel are used.

For peristaltic pumping, mixing, and flow regulation, lesser extensions relative to channel height are useful. The areal size of the tactile activators may vary appropriately with channel width and function, and may range from 40 µm to about 2 mm. Larger and smaller sizes are possible as well.

Appendix A discloses a handheld recirculation system and customized media for microfluidic cell culture. Appendix B discloses a device for embryo culture and use thereof. Appendix C discloses integrated microfluidic control employing programable tactile actuators. Appendix D discloses a computerized control method and system for microfluidics and computer program product for use therein. Embodiments of the invention may take the form of embodiments, or portions of embodiments, described in Appendices A, B, C, and D.

Appendix A

Many modifications of the present invention will be apparent to those skilled in the art, and are part of the subject matter disclosed herein. The clamping mechanism, for example, may be replaced or augmented by other clamping mechanisms, including simple clamps which are separate from but engageable with the fingerplate, or which can span the height of the entire device, including the braille display module.

In similar manner, while the transparent heating element is described as being fabricated on a glass slide, it will be appreciated that this glass slide may be incorporated into a disposable device, become an integrated part thereof rather than a separate device. While less favorable, the heating element may also be disposed directly on the microfluidics chip. The heating unit may also be patterned such that only portions of the glass slide or chip are heated, thus conserving electrical power as well as avoiding heat in areas where heating is not desired, for example in fluid storage areas.

In advanced versions of the present lab-on-chip, it is desirable to have a battery power supply, either one-time use or rechargeable, on the chip itself, together with electrical circuitry for controlled operation of the heater unit, and of the tactile actuators also, when this is desired. The ability to divorce the structure from corded power supplies allows the module to be easily transported to other stations for testing, analysis, etc., while preserving the microenvironment within the module.

The subject invention further pertains to PMDS or other elastomeric silicone structures which incorporate a film, coating, or membrane over all or only a portion of the module structure, which serves as a vapor barrier to minimize evaporation of liquids contained in the channels, reservoirs, etc., of the devices. Suitable vapor barriers are, in general, relatively pore free, hydrophobic films, e.g. of parylene. In addition, films which are resistant to the flow of oxygen, of carbon dioxide, or both these gases may also be applied to minimize any influence of the ambient atmosphere on the conditions established within the device. Such films are well known from the field of plastic, particularly polyethylene terephthalate, drink containers.

Appendix B

It has now been surprisingly discovered that embryos may be grown with good survival rates in an efficient manner by growth at the bottom of a well which is in communication with a microchannel device supplying fluid to the well proximate its bottom. The bottom opening is sized so as not to allow the embryo to enter the channel.

The invention may be described with relation to the accompanying drawings, many of which illustrate the volumes or hollows, channels, etc. within the microfluidics device rather than the walls of the device themselves. As illustrated, the best mode of the device is a generally conical well which at its tip has an opening which communicates with one or a plurality of microchannels. The well is filled with fluid, as are the microchannels, and one or more embryos are introduced into the well, for example by pipet. The embryos settle to the bottom, but are prevented from exiting the well due to them being larger than the holes in the well.

Fluid may be introduced into the well continuously or discontinuously, the fluid preferably containing the necessary growth media for the embryo. For example, in a well with a single hole at the bottom, fluid may be caused to rise in the well from the microchannels, introducing extra nutrients, and then to fall, removing fluid which now contains exogenous substances (waste) via the microchannels.

Introduction and removal of fluid can be made using conventional gravity pumps, or constant flow gravity driven pumps. Fluid can also be supplied by outside supplies such as pumps, etc., or preferably by on-board or "semi-on board" tactile actuator-based pumping systems.

The well can also have inlets at other locations and or heights rather than exclusively at the bottom, so long as the entrance ways to the channels are sized such that the embryos will not pass into the channels. For example, there might be an opening at the bottom of the well and an opening near the middle or top, with fluid being supplied at the bottom, for example, and being removed closer to the top.

The well also need not be entirely conical in shape, but is preferably shaped such that the walls are inclined, regardless of whether linear or curved such that the embryo's will have a natural tendency to gravitate toward the bottom and center of the well. The material of the well is not overly critical, and may be thermosetting resin or thermoplastic, metal, glass, ceramic, etc. In preferred constructions, the device is a multilayer device, the top layer containing the well, and constructed of relatively rigid material so as to provide support for elastomeric layers or layers of lesser strength and/or modulus below.

Thus, it is preferable that the top layer be of hard transparent material such as glass, polymethylmethacrylate, etc. The conical well should have a low surface roughness, preferably below 5 μm Ra, more preferably less than 1 μm Ra, and yet more preferably less than 0.1 μm Ra.

In preferred devices, the conical well penetrates entirely through the top layer, thus having an open, wide-mouthed end on one side of the top layer, and on the bottom this layer, a relatively narrow hole which allows fluid communication with the microchannels in the second layer. The second layer preferably directly abuts the first layer, and has one or a plurality of microchannels which are in fluid communication with the conical well. It is relatively important that the channels be positioned closely with respect to the opening in the well. For example misalignment should preferably be maximized at 50 μm. The second layer may also constitute the bottom layer, particularly when the microfluid channels are substantially on top of the second layer, i.e. abutting the bottom surface of the top layer. However, in preferred devices, the channels are at least in part along the bottom of the second layer and a third, or sealing layer is applied thereto. This sealing layer is preferably rather thin, such that brailletype tactile actuators may act as valves and pumps for the various microchannels. By this means, for example, fluid can be caused to flow or to be pumped in only one direction in a given microchannel, or can be bidirectional flow, depending upon the valving, whether the valves are on or off, and whether a pump is pumping one way or the other with respect to the channel.

In use, the device is first filled with fluid, for example an embryo culture medium, and one or more embryos added to the well, An oil overlay, produced by dropping one or two fine drops of oil onto the liquid surface in the well is then provided. The oil prevents evaporation of liquid from the well, thus changing the osmolality, or concentration, of the ingredients therein. It also affects the flow of air, including specifically oxygen and $CO_2$ into the fluid, and the release of these gases from the fluid. The oil may be any compatible oil, for example a silicone oil, a paraffin oil, a polyethylene oligomer oil, etc. For the same reason, portions of the apparatus in the second and/or third layers may be coated, for example with parylene or other coating which minimizes, particularly, water loss.

The second and third layers are preferably made of cast elastomer, particularly when the valving and pumping embodiments employing tactile actuators are employed. However, if "off-chip" fluid supply, valving, etc. is used, then use of an elastomer is not necessary, and other materials such as cast epoxy, injection molded thermoplastic, glass, etc., can be used. It is of course recognized that the surface of these materials should be compatible with embryo culture, and if not, should be coated appropriately.

The process of the subject invention requires introduction of zygote(s) into the well which contains fluid, preferably a growth fluid as is conventionally employed for embryo culture. The fluid in the conical well is then covered with oil, preferably mineral oil, and the device incubated at a suitable temperature. Fluid is directed into and out of the well through the microchannels continuously or discontinuously. For example, a back and forth type of fluid supply wherein the fluid level in the well increases and then decreases cyclically has been found most advantageous. The growing embryo may be inspected by conventional optical microscopy methods, and when judged grown to the proper stage, the embryo is removed from the well. Because the top of the well is larger then the bottom, removal is particularly easy and the risk of damage is low.

Appendix C

The microfluidic devices of the present invention contain microchannels whose flow characteristics are to be actively varied, formed in a compressible or distortable elastomeric material. Thus, it is preferred that substantially the entire microfluidic device be constructed of a flexible elastomeric material such as an organopolysiloxane elastomer ("PDMS"), as described hereinafter. However, the device substrate may also be constructed of hard, i.e., substantially non-elastic material at portions where active control is not desired, although such construction generally involves added construction complexity and expense. The generally planar devices preferably contain a rigid support of glass, silica, rigid plastic, metal, etc. on one side of the device to provide adequate support, although in some devices, actuation from both major surfaces may require that these supports be absent, or be positioned remote to the elastomeric device itself.

The microfluidic devices of the present invention contain at least one active portion which alters the shape and/or volume of chambers or passageways ("empty space"), particularly fluid flow capabilities of the device. Such active portions include, without limitation, mixing portions, pumping portions, valving portions, flow portions, channel or reservoir selection portions, cell crushing portions, unclogging portions, etc. These active portions all induce some change in the fluid flow, fluid characteristics, channel or reservoir characteristics, etc. by exerting a pressure on the relevant portions of the device, and thus altering the shape and/or volume of the empty space which constitutes these features. The term "empty space" refers to the absence of substrate material. In use, the empty space is usually filled with fluids, microorganisms, etc.

The active portions of the device are activatable by pressure to close their respective channels or to restrict the cross-sectional area of the channels to accomplish the desired active control. To achieve this purpose, the channels, reservoirs, etc. are constructed in such a way that modest pressure from the exterior of the microfluidic device causes the channels, reservoirs, etc. ("microfluidic features") to compress, causing local restriction or total closure of the respective feature. To accomplish this result, the walls within the plane of the device surrounding the feature are preferably elastomeric, and the external surfaces (e.g., in a planar device, an outside major surface) are necessarily elastomeric, such that a minor amount of pressure causes the external surface and optionally the internal feature walls to distort, either reducing cross-sectional area at this point or completely closing the feature.

The pressure required to "activate" the active portion(s) of the device is supplied by an external tactile device such as are used in refreshable Braille displays. The tactile actuator contacts the active portion of the device, and when energized, extends and presses upon the deformable elastomer, restricting or closing the feature in the active portion.

Rather than close or restrict a feature by being energized, the tactile actuator may be manufactured in an extended position, which retracts upon energizing, or may be applied to the microfluidics device in an energized state, closing or restricting the passage, further opening the passage upon de-energizing.

The preferred actuators at the present time are programmable Braille display devices such as those previously commercially available from Telesensory as the Navigator.TM. Braille Display with Gateway.TM. software which directly translates screen text into Braille code. These devices generally consist of a linear array of "8-dot" cells, each cell and each cell "dot" of which is individually programmable. Such devices are used by the visually impaired to convert a row of text to Braille symbols, one row at a time, for example to "read" a textual message, book, etc. These devices are presently preferred because of their ready commercial availability. The microfluidic device active portions are designed such that they will be positionable below respective actutable "dots" or protrusions on the Braille display. Braille displays are available from Handy Tech, Blazie, and Alva, among other suppliers.

However, to increase flexibility, it is possible to provide a regular rectangular array usable with a plurality of microfluidics devices, for example having a 10.times.10, 16.times.16, 20.times.100, 100.times.100, or other array. The more close the spacing and the higher the number of programmable extendable protrusions, the greater is the flexibility in design of microdevices. Production of such devices follows the methods of construction known in the art. Addressability also follows from customary methods. Non-regular arrays, i.e. in patterns having actuators only where desired are also possible.

Suitable Braille display devices suitable for non-integral use are available from Handy Tech Electronik GmbH, Horb, Germany, as the Graphic Window Professional.TM. (GWP), having an array of 24.times.16 tactile pins. Pneumatic displays operated by microvalves have been disclosed by Orbital Research, Inc. said to reduce the cost of Braille tactile cells from 70 $ U.S. per cell to Ca. 5-10 $/cell. Piezoelectric actuators are also usable where a piezoelectric element replaces the electrorheological fluid, and electrode positioning is altered accordingly.

The microfluidic devices of the present invention have many uses. In cell growth, the nutrients supplied may need to be varied to simulate availability in living systems. By providing several supply channels with active portions to close or restrict the various channels, supply of nutrients and other fluids may be varied at will. An example is a three dimensional scaffolding system to create bony tissue, the scaffolding supplied by various nutrients from reservoirs, coupled with peristaltic pumping to simulate natural circulation.

A further application involves cell crushing. Cells may be crushed by transporting them in channels through active portions and actuating channel closure to crush the cells flowing through the channels. Cell detection may be achieved, for example, by flow cytometry techniques using transparent microfluidic devices and suitable detectors. Embedding optical fibers at various angles to the channel can facilitate detection and activation of the appropriate activators. Similar detection techniques, coupled with the use of valves to vary the delivery from a channel to respective different collection sites or reservoirs can be used to sort embryos and microorganisms, including bacteria, fungi, algae, yeast, viruses, sperm cells, etc.

Growth of embryos generally require a channel or growth chamber which is capable of accommodating the embryo and allowing for its subsequent growth. Such deep channels cannot effectively be closed, however. A microfluidics device capable of embryo growth may be fabricated by multiexposure photolithography, using two masks. First, a large, somewhat rectangular (200 .mu.m width.times.200 .mu.m depth) channel, optionally with a larger 200 .mu.m deep by 300 .mu.m length and 300 .mu.m width growth chamber at one end is fabricated. Merging with the 200 .mu.m.times.200 .mu.m channel is a smaller channel with a depth of ca. 30 .mu.m, easily capable of closure by a Braille pin. Exiting the bulbous growth chamber are one or more thin (30 .mu.m) channels. In operation, embryo and media are introduced into the large channel and travel to the bulbous growth chamber. Because the exit channels from the growth chamber are very small, the embryo is trapped in the chamber. The merging channels and exit channels can be used to supply nutrients, etc., in any manner, i.e. continuous, pulsating, reverse flow, etc. The embryo may be studied by spectroscopic and/or microscopic methods, and may be removed by separating the elastomeric layer covering the PDMS body which houses the various channels.

Construction of fluidic devices is preferably performed by soft lithography techniques, as described, for example by D. C. Duffy et al., Rapid Prototyping of Microfluidic Systems in Poly(dimethylsiloxane), ANALYTICAL CHEMISTRY 70, 4974-4984 (1998). See also, J. R. Anderson et al., ANALYTICAL CHEMISTRY 72, 3158-64 (2000); and M. A. Unger et al., SCIENCE 288, 113-16 (2000). Addition-curable RTV-2 silicone elastomers such as SYLGARD.RTM. 184, Dow Corning Co., can be used for this purpose.

The dimensions of the various flow channels, reservoirs, growth chambers, etc. are easily determined by volume and flow rate properties, etc. Channels which are designed for complete closure must be of a depth such that the elastomeric layer between the microchannel and the actuator can approach the bottom of the channel. Manufacturing the substrate of elastomeric material facilitates complete closure, in general, as does also a cross-section which is rounded, particularly at the furthest corners (further from the actuator). The depth will also depend, for example, on the extension possible for the actuator's extendable protrusions. Thus, channel depths may vary quite a bit. A depth of less than 100 .mu.m is preferred, more preferably less than 50 .mu.m. Channel depths in the range of 10 .mu.m to 40 .mu.m are preferred for the majority of applications, but even very low channel depths, i.e. 1 nm are feasible, and depths of 500 .mu.m are possible with suitable actuators, particularly if partial closure ("partial valving") is sufficient.

The substrate may be of one layer or a plurality of layers. The individual layers may be prepared by numerous techniques, including laser ablation, plasma etching, wet chemical methods, injection molding, press molding, etc. However, as indicated previously, casting from curable silicone is most preferred, particularly when optical properties are important. Generation of the negative mold can be made by numerous methods, all of which are well known to those skilled in the art. The silicone is then poured onto the mold, degassed if necessary, and allowed to cure. Adherence of multiple layers to each other may be accomplished by conventional techniques.

A preferred method of manufacture of some devices employs preparing a master through use of a negative photoresist. SU-8 50 photoresist from Micro Chem. Corp., Newton, Mass., is preferred. The photoresist may be applied to a glass substrate and exposed from the uncoated side through a suitable mask. Since the depth of cure is dependant on factors such as length of exposure and intensity of the light source, features ranging from very thin up to the depth of the photoresist may be created. The unexposed resist is removed, leaving a raised pattern on the glass substrate. The curable elastomer is cast onto this master and then removed.

The material properties of SU-8 photoresist and the diffuse light from an inexpensive light source can be employed to generate microstructures and channels with cross-sectional profiles that are "rounded and smooth" at the edges yet flat at the top (i.e. bell-shaped). Short exposures tend to produce a radiused top, while longer exposures tend to produce a flat top with rounded corners. Longer exposures also tend to produce wider channels. These profiles are ideal for use as compressive, deformation-based valves that require complete collapse of the channel structure to stop fluid flow, as disclosed by M. A. Unger, et al., SCIENCE 2000, 288, 113. With such channels, Braille-type actuators produced full closure of the microchannels, thus producing a very useful valved microchannel. Such shapes also lend themselves to produce uniform flow fields, and have good optical properties as well.

In a typical procedure, a photoresist layer is exposed from the backside of the substrate through a mask, for example photoplotted film, by diffused light generated with an ultraviolet (UV) transilluminator. Bell-shaped cross-sections are generated due to the way in which the spherical wavefront created by diffused light penetrates into the negative photoresist. The exposure dose dependent change in the SU-8 absorption coefficient (3985 m.sup.−1 unexposed to 9700 m.sup.−1 exposed at 365 nm) limits exposure depth at the edges.

The exact cross-sectional shapes and widths of the fabricated structures are determined by a combination of photomask feature size, exposure time/intensity, resist thickness, and distance between the photomask and photoresist. Although backside exposure makes features which are wider than the size defined by the photomask and in some cases smaller in height compared to the thickness of the original photoresist coating, the change in dimensions of the transferred patterns is readily predicted from mask dimensions and exposure time. The relationship between the width of the photomask patterns and the photoresist patterns obtained is essentially linear (slope of 1) beyond a certain photomask aperture size. This linear relationship allows straightforward compensation of the aperture size on the photomask through simple subtraction of a constant value. When exposure time is held constant, there is a threshold aperture size below which incomplete exposure will cause the microchannel height to be lower than the original photoresist thickness. Lower exposure doses will make channels with smoother and more rounded cross-sectional profiles. Light exposure doses that are too slow (or photoresist thicknesses that are too large), however, are insufficient in penetrating through the photoresist, resulting in cross-sections that are thinner than the thickness of the original photoresist.

The suitability of bell-shaped cross-section microchannels of 30 .mu.m thickness to be used as deformation-based valves was evaluated by exerting an external force onto the channel using a piezoelectric vertical actuator of commercially available refreshable Braille displays. Spaces may be left between the membrane and the wall when the channel cross-section has discontinuous tangents, such as in rectangular cross-sections. In contrast, a channel with a bell-shaped cross-section is fully closed under the same conditions. When a Braille pin is pushed against a bell-shaped or rectangular-shaped cross-section microchannel through a 200 .mu.m poly(dimethylsiloxane) (PDMS) membrane, the bell-shaped channels were fully closed while the rectangular channels of the same width had considerable leakage.

The technique described is cost- and time-effective compared to other photolithographic methods for generating well defined rounded profiles such as gray-scale mask lithography, or laser beam polymerization because there is no need for special equipment such as lasers, collimated light sources (mask aligner), or submicron resolution photomasks; it only requires a transilluminator available in many biological labs. In addition, the backside exposure technique can generate more profiles compared to other soft lithography-based patterning methods such as microfluidic mask lithography and the use of patterned laminar flows of etchant in an existing microchannel.

When used as deformation-based microfluidic valves, these bell-shaped microchannels showed improved self-sealing upon compression compared to conventional rectangular or semi-circular cross-section channels as demonstrated by simulations, and by experiments. A bell-shaped channel (width: 30 .mu.m; height 30 .mu.m) was completely closed by an 18 gf-force squeeze of a Braille pin. It is notable that channels that have the bell-shaped cross-sections with "gently sloping" sidewalls cannot be fabricated by melting resist technology, one of the most convenient methods to fabricate photomask-definable rounded patterns, because the profile is determined by surface tension. The bell-shaped channels maximize the cross-sectional area within microfluidic channels without compromising the ability to completely close channels upon deformation. For example, the channel cross-section described here is larger than previously reported, pneumatically actuated deformation-based valves (100 .mu.m in width; 201 m in height) and may be more suitable for mammalian cell culture. Furthermore, the bell-shaped cross-sections provide channels with flat ceilings and floors, which is advantageous for reducing aberrations in optical microscopy and in obtaining flow fields with a more uniform velocity profile across the widths of the channel. These advantages of microchannels with bell-shaped cross-sectional shapes combined with the convenient, inexpensive, and commercially available valve actuation mechanism based on refreshable Braille displays will be useful for a wide range of microfluidic applications such as microfluidic cell culture and analysis systems, biosensors, and on-chip optical devices such as microlenses.

The extension outwards of the tactile actuators must be sufficient for their desired purpose. Complete closure of a 40 .mu.m deep microchannel, for example, will generally require a 40 .mu.m extension ("protrusion") or more when a single actuator is used, and about 20 .mu.m or more when dual actuators on opposite sides of the channel are used. For peristaltic pumping, mixing, and flow regulation, lesser extensions relative to channel height are useful. The areal size of the tactile activators may vary appropriately with channel width and function (closure, flow regulation, pumping, etc.), and may preferably range from 40 .mu.m to about 2 mm, more preferably 0.5 mm to 1.5 mm. Larger and smaller sizes are possible as well. The actuators must generate sufficient force. The force generated by one Braille-type display pin is approximately 176 mN, and in other displays may be higher or lower.

By use of the present invention, numerous functions can be implemented on a single device. Use of multiple reservoirs for supply of nutrients, growth factors, etc. is possible. The various reservoirs make possible any combination of fluid supply, i.e. from a single reservoir at a time, or from any combination of reservoirs. This is accomplished by establishing fluid communication with a reservoir by means of a valved microchannel, as previously described. By programming the Braille display or actuator array, each individual reservoir may be connected with a growth channel or chamber at will. By also incorporating a plurality of extendable protrusions along a microchannel supply, peristaltic pumping may be performed at a variety of flow rates. Uneven, pulsed flow typical of vertebrate circulatory systems can easily be created. Despite the flexibility which the inventive system offers, construction is straightforward. The simplicity of the microfluidics device per se, coupled with a simple, programmable external actuator, enables a cost-effective system to be prepared, where the microfluidic device is relatively inexpensive and disposable, despite its technological capabilities.

Combinatorial, regulated flow with multiple pumps and valves that offer more flexibility in microfluidic cell studies in a laptop to handheld-sized system are created by using a grid of tiny actuators on refreshable Braille displays. These displays are typically used by the visually impaired as tactile analogs to computer monitors. Displays usually contain 20-80 rows of cells, each holding 8 (4.times.2) vertically moving pins (.about.1-1.3 mm). Two pins on the same cell may typically be 2.45 mm apart center to center and 3.8 mm apart on different cells. Each pin may have the potential to protrude 0.7.about.1 mm upward using piezoelectric mechanisms, and may hold up to .about.15-20 cN. Control of Braille pins actuators is accomplished by changing a line of text in a computer program. Unique combinations of Braille pins will protrude depending on the letters displayed at a given time. Braille displays are pre-packaged with software, easy to use, and readily accessible. They are designed for individual use, and range from walkman to laptop sizes while using AC or battery power. By using the moving Braille pins against channels in elastomeric, transparent rubber, it is possible to deform channels and create in situ pumps and valves.

Appendix D

Embodiments of microfluidic devices may be suitable for the culture of a living organism in a fluid. A microfluidic device may control the flow and composition of fluids provided to the living organism. The microfluidic device may provide laminar, pseudo-multiple laminar or non-laminar flows. The microfluidic device may perform physical operations on the living organism. The microfluidic device may be used, for example, for general cell culture including cell washing and detachment, cell seeding and culture. The microfluidic device may be used as a microreactor, a tissue culture device, a cell culture device, a cell sorting device, a cell crushing device, a micro flow cytometer, a motile sperm sorter, a micro carburetor, a micro spectrophotometer, or a microscale tissue engineering device. The microfluidic device may includes sensors to determine states or flow characteristics of elements of the microfluidic device or the passage of particles in a channel. The sensors may be, for example, optical, electrical, or electromechanical sensors.

In one embodiment, a microfluidic device includes microchannels having flow characteristics that are actively varied and formed in a compressible or distortable elastomeric material. In one embodiment, the entire microfluidic device is constructed of a flexible elastomeric material, such as an organopolysiloxane elastomer ("PDMS"), as described hereinafter. However, the device substrate may also be constructed of hard, e.g., substantially non-elastic material at portions, where active control is not desired.

The microfluidic devices may contain at least one active portion that alters the shape and/or volume of chambers or passageways ("empty space"), particularly fluid flow capabilities of the device. Such active portions include, without limitation, mixing portions, pumping portions, valving portions, flow portions, channel or reservoir selection portions, cell crushing portions, and unclogging portions. These active portions all induce some change in the fluid flow, fluid characteristics, channel or reservoir characteristics, by exerting a pressure on the relevant portions of the device, and thus altering the shape and/or volume of the empty space which constitutes these features. The term "empty space" refers to the absence of substrate material. In use, the empty space is usually filled with fluids or microorganisms.

The active portions of the device are activatable by pressure to close their respective channels or to restrict the cross-sectional area of the channels to accomplish the desired active control. To achieve this purpose, the channels, reservoirs, or other elements are constructed in such a way that modest pressure from the exterior of the microfluidic device causes the channels, reservoirs or other elements ("microfluidic features") to compress, causing local restriction or total closure of the respective feature. To accomplish this result, the walls within the plane of the device surrounding the feature are preferably elastomeric, and the external surfaces (e.g., in a planar device, an outside major surface) are elastomeric, such that a minor amount of pressure causes the external surface and optionally the internal feature walls to distort, either reducing cross-sectional area at this point or completely closing the feature.

The pressure used to "activate" the active portion(s) of the device is supplied by an external tactile device, such as are used in refreshable Braille displays of the actuator system. The tactile actuator contacts the active portion of the device, and when energized, extends and presses upon the deformable elastomer, restricting or closing the feature in the active portion.

In some embodiments, rather than close or restrict a feature by being energized, the tactile actuator may be manufactured in an extended position, which retracts upon energizing, or may be applied to the microfluidic device in an energized state, closing or restricting the passage, further opening the passage upon de-energizing.

A significant improvement in the performance, not only of the subject invention devices, but of other microfluidic devices which use pressure, e.g., pneumatic pressure, to activate device features, may be achieved by molding the device to include one or more voids adjacent the channel walls. These voids allow for more complete closure or distortion of the respective feature.

In one embodiment, the actuator system is a programmable Braille display that includes a plurality of moveable pins that each engage a corresponding element of the microfluidic device to perform a fluidic operation. The elements of the microfluidic device include pumps and valves. The pins may be arranged in a regular geometric array. Such arrangement maybe used with different configurations of the microfluidic device. In this arrangement, some pins may not be used for particular microfluidic devices because no element in the device corresponds to the pin. Alternatively the pins may be selected to correspond to elements of a specific or a group of multifluidic devices. Each pin may be controlled independently, and individually addressable.

An example of an actuator system is a Telesensory system such as the Navigator™ Braille Display with Gateway™ software, which directly translates screen text into Braille code. These devices generally comprise a linear array of "8-dot" cells, each cell and each cell "dot" of which is individually programmable. Such devices are used by the visually impaired to convert a row of text to Braille symbols, one row at a time, for example to "read" a textual message or book. The microfluidic device active portions are designed such that they will be positionable below respective actuable "dots" or protrusions on the Braille display. Braille displays are available from Handy Tech, Blazie, and Alva, among other suppliers. As will be described below, the system may use various software programs for controlling the pins of the actuator system by allowing the user to select processes to be performed on the organism, and then executing processes from a library.

However, to increase flexibility, it is possible to provide a regular rectangular array usable with a plurality of microfluidic devices, for example having a 10×10, 16×16, 20×100, 100×100 or other size array. The closer the spacing and the higher the number of programmable extendable protrusions, the greater is the flexibility in design of microdevices. Production of such devices follows the methods of construction known in the art. Addressability also follows from customary methods. Non-regular arrays, e.g., in patterns having actuators only where desired are also possible.

Devices can also be constructed which integrate the tactile actuators with the microfluidic device. The actuators are still located external to the microfluidic device itself, but attached or bonded thereto to form an integrated whole. Other types of actuator systems may be used, such as a tactile actuator device, which employs a buildup of an electrorheological fluid, an electromechanical Braille-type device employing shape memory wires for displacement between "on" and "off" portions, devices employing electrorheologic or magnetorheologic working fluids or gels, a pneumatically operated Braille device, "voice coil" type structures, especially those employing strong permanent magnets, devices employing shape memory alloys and intrinsically conducting polymer sheets.

Suitable Braille display devices suitable for non-integral use are available from Handy Tech Electronik GmbH, Horb, Germany, as the Graphic Window Professional™ (GWP), having an array of 24×16 tactile pins. Piezoelectric actuators are also usable where a piezoelectric element replaces the electrorheological fluid, and electrode positioning is altered accordingly.

The microfluidic device has many uses. The software described herein automates the operation of these uses. In cell growth, the nutrients supplied may be varied to simulate availability in living systems. By providing several supply channels with active portions to close or restrict the various channels, supply of nutrients and other fluids may be varied at will. An example is a three dimensional scaffolding system to create bony tissue, the scaffolding supplied by various nutrients from reservoirs, coupled with peristaltic pumping to simulate natural circulation.

Another application involves cell crushing. Cells may be crushed by transporting them in channels through active portions and actuating channel closure to crush the cells flowing through the channels. Cell detection may be achieved, for example, by flow cytometry techniques using transparent microfluidic devices and suitable detectors. Embedding optical fibers at various angles to the channel can facilitate detection and activation of the appropriate activators. Similar detection techniques, coupled with the use of valves to vary the delivery from a channel to respective different collection sites or reservoirs can be used to sort embryos and microorganisms, including bacteria, fungi, algae, yeast, viruses, and sperm cells.

The software controls the actuator system to control the pressure and thus the opening and closing of the channel and the timing. Depending on the processes to be performed, the software may address the actuators individually or in groups, and in patterns to provide actions, such as a peristaltic pumping action or a mixing action with respect to fluid in the channel. The software may monitor the sensors of the microfluidic device to selectively control the channel flow.

As an illustrative example of peristaltic pump formed by three pins engaging the microfluidic device, a pattern, such as XXO, OXX, OOX, XOX in repetition, where X is a closed position and O is an open position, to pump fluid in a channel may be used. The resultant fluid flow is pulsatile, with transient movements in both directions. The net movement can be predicted by its linear relationship to the pattern change frequency, and flow direction can be switched by reversing the pattern of actuation.

By use of the present invention, numerous functions can be implemented on a single device. Use of multiple reservoirs for supply of nutrients, growth factors, and the like is possible. The various reservoirs make possible any combination of fluid supply, e.g., from a single reservoir at a time, or from any combination of reservoirs. This is accomplished by establishing fluid communication with a reservoir by means of a valved microchannel, as previously described. By programming the actuator system, each individual reservoir may be connected with a growth channel or chamber at will. By also incorporating a plurality of extendable protrusions along a microchannel supply, peristaltic pumping may be performed at a variety of flow rates. Uneven, pulsed flow typical of vertebrate circulatory systems can easily be created. Combinatorial, regulated flow with multiple pumps and valves that offer more flexibility in microfluidic cell studies are created by using a grid of tiny actuators on refreshable Braille displays and executed automatically by software in response to user selections of processes to be performed.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method, comprising:
   a) providing a substrate comprising
      a reservoir formed in the substrate and having upper and lower portions, the upper portion being sized to permit the insertion and removal of a cell mass from the reservoir; and
      a passage at least partially formed in the substrate and in fluid communication with the reservoir wherein a surface of the passage comprises a deformable membrane comprising a plurality of layers, wherein a first layer comprises a deformable elastomer and a second layer comprises a non-rigid polymer that blocks moisture;
   b) inserting a cell mass in a reservoir of said substrate under conditions, wherein said lower portion of said reservoir has a width less than 250 micrometers to retain at least a portion of the cell mass within the lower portion of the reservoir, wherein said cell mass is prevented from entering said passage and the cell mass can be directly removed from the lower portion through the upper portion; and
   c) culturing said cell mass in said reservoir such that said cell mass grows.

2. The method of claim 1, wherein the cell mass is selected from the group consisting of a denuded human zygote, a denuded mammalian zygote, a clump of mammalian cells, and a single mammalian cell.

3. The method of claim 1, wherein the passage adjacent the lower portion has a passage width and a passage height and wherein at least one of the passage height and the passage width has a length selected from the group consisting of less than 500 micrometers, less than 250 micrometers, less than 140 micrometers, less than 70 micrometers, less than 50 micrometers, and less than 5 micrometers to retain at least a portion of the cell mass within the reservoir.

4. The method of claim 1, wherein the lower portion of the reservoir has a width selected from the group consisting of less than 140 micrometers, less than 70 micrometers, less than 50 micrometers, and less than 5 micrometers.

5. The method of claim 2, wherein said cell mass is a denuded human zygote.

6. The method of claim 2, wherein said cell mass is a denuded mammalian zygote.

7. The method of claim 1, wherein said reservoir and said passage comprise a fluid.

8. The method of claim 7, further comprising the step of moving said fluid from said passage to said reservoir by deforming said deformable membrane.

9. The method of claim 1, wherein said non-rigid polymer is parylene, polyvinylidene chloride or polyurethane.

10. The method of claim 1, wherein said deformable elastomer is PDMS.

11. The method of claim 2, wherein said cell mass is a denuded human zygote and said lower portion of said reservoir has a width less than 140 micrometers.

12. The method of claim 2, wherein said cell mass is a denuded mammalian zygote and said lower portion of said reservoir has a width less than 70 micrometers.

13. The method of claim 2, wherein said cell mass is a single mammalian cells and said lower portion of said reservoir has a width less than 5 micrometers.

* * * * *